(12) United States Patent
Huang et al.

(10) Patent No.: US 9,968,606 B2
(45) Date of Patent: May 15, 2018

(54) DEUTERATED COMPOUNDS FOR TREATING CANCER AND RELATED DISEASES AND CONDITIONS, AND COMPOSITIONS AND METHODS THEREOF

(71) Applicant: NeuForm Pharmaceuticals, Inc., Framingham, MA (US)

(72) Inventors: Chaoran Huang, Auburndale, MA (US); Changfu Cheng, Northborough, MA (US)

(73) Assignee: NeuForm Pharmaceuticals, Inc., Auburndale, MA (US)

( * ) Notice: Subject to any disclaimer, the term of this patent is extended or adjusted under 35 U.S.C. 154(b) by 0 days. days.

(21) Appl. No.: 15/599,415

(22) Filed: May 18, 2017

(65) Prior Publication Data

US 2017/0368065 A1 Dec. 28, 2017

Related U.S. Application Data

(63) Continuation of application No. PCT/US2016/068585, filed on Dec. 23, 2016.

(60) Provisional application No. 62/271,275, filed on Dec. 27, 2015, provisional application No. 62/330,810, filed on May 2, 2016.

(51) Int. Cl.
| | |
|---|---|
| *A61K 31/506* | (2006.01) |
| *C07B 59/00* | (2006.01) |
| *A61K 31/404* | (2006.01) |
| *A61K 31/085* | (2006.01) |
| *A61K 31/167* | (2006.01) |
| *A61K 31/035* | (2006.01) |
| *G01R 33/46* | (2006.01) |
| *G01N 30/02* | (2006.01) |

(52) U.S. Cl.
CPC .......... *A61K 31/506* (2013.01); *A61K 31/035* (2013.01); *A61K 31/085* (2013.01); *A61K 31/167* (2013.01); *A61K 31/404* (2013.01); *C07B 59/002* (2013.01); *G01N 2030/027* (2013.01); *G01R 33/46* (2013.01)

(58) Field of Classification Search
CPC .. A61K 31/506; A61K 31/085; A61K 31/035; A61K 31/167; A61K 31/404; C07B 59/00; G01R 33/46; G01N 30/02
See application file for complete search history.

(56) References Cited

FOREIGN PATENT DOCUMENTS

WO 2016023422 * 2/2016

* cited by examiner

*Primary Examiner* — Alexander R Pagano
*Assistant Examiner* — Ebenezer Sackey
(74) *Attorney, Agent, or Firm* — Milstein Zhang & Wu LLC

(57) ABSTRACT

The invention provides novel chemical compounds useful for treating cancer or a related disease or disorder thereof, and pharmaceutical composition and methods of preparation and use thereof.

29 Claims, 14 Drawing Sheets

DEUTERATED COMPOUNDS FOR TREATING CANCER AND RELATED DISEASES AND CONDITIONS, AND COMPOSITIONS AND METHODS THEREOF

PRIORITY CLAIMS AND RELATED PATENT APPLICATIONS

This application claims the benefit of priority to PCT/US16/68585, filed Dec. 23, 2016, which claims the benefit of priority to U.S. Provisional Application Ser. No. 62/271,275, filed on Dec. 27, 2015, and Ser. No. 62/330,810, filed on May 2, 2016, the entire content of each of which is incorporated herein by reference in its entirety.

TECHNICAL FIELDS OF THE INVENTION

The invention generally relates to therapeutics and treatment methods for certain diseases and conditions. More particularly, the invention provides novel chemical compounds, including N-(2-{2-dimethylaminoethyl-methylamino}-4-methoxy-5-{[4-(1-methylindol-3-yl)pyrimidin-2-yl]amino}phenyl)prop-2-enamide with one or more deuterium-substitutions at strategic positions, that are epidermal growth factor receptor tyrosine kinase inhibitors (EGFR-TKIs) and are useful for treating various forms of cancer, e.g., non-small cell lung cancer (NSCLC), or related diseases and conditions, and pharmaceutical compositions and methods of preparation and use thereof.

BACKGROUND OF THE INVENTION

Cancer is a group of diseases involving the development of abnormal cells that divide uncontrollably and have the ability to infiltrate and destroy normal body tissue. It is the second-leading cause of death in the United States. Common types of cancer include lung cancer, prostate cancer, breast cancer, colorectal cancer, and cervical cancer. Although treatment options for cancer patients have increased steadily over the past decades, including surgery, chemotherapy, radiation therapy, hormonal therapy, targeted therapy and palliative care, cancer remains a top health threat and is responsible for about 15% of all human deaths.

Lung cancer is the second most common cancer, accounting for about 13% of all new cancer cases and account for around 27% of mortality of all cancers. NSCLC is the most common type of lung cancer. About 85%-90% of lung cancers are non-small cell lung cancers, which are histologically divided into sub-types of squamous cell carcinoma, adenocarcinoma, and large cell carcinoma.

Treatment options for NSCLC are limited and often come with undesirable side effects. NSCLC remains one of the most difficult cancers to treat effectively. EGFR mutations occur in about 30% to 40% of NSCLCs in Asian patients and in about 15% of NSCLCs in western patients. First generation EGFR-TKIs, such as gefitinib and erlotinib, represent the best therapeutic option in first, second and maintenance setting for EGFR mutant patients. Virtually all patients, however, develop acquired resistance and, despite an initial benefit, progress due to the development of resistance. Among the molecular mechanisms responsible for acquired resistance are up-regulation of the downstream signal by mesenchymal-epidermal transition (MET) amplification and the emergence of T790M EGFR gatekeeper mutation. EGFR T790M mutation is responsible for resistance in around 60% of cases.

There is an urgent and growing need for innovative cancer therapeutics and treatment methods that can overcome acquired resistance, in particular resistance due to EGFR T790M mutation, leading to improved clinical effectiveness with reduced side effects.

SUMMARY OF THE INVENTION

The invention provides novel chemical entities that may be used to treat cancer (e.g., NSCLC). These compounds are biochemically potent and physiologically active with improved pharmacokinetic, therapeutic and toxicological properties over N-(2-{2-dimethylaminoethyl-methylamino}-4-methoxy-5-{[4-(1-methylindol-3-yl)pyrimidin-2-yl]amino}phenyl)prop-2-enamide. The compounds disclosed herein are deuterium-substituted versions of this compound, where one or more hydrogen atoms are substituted with deuterium at strategic locations of the molecule. Such strategic deuterium substitution leads to positive impact on the pharmacokinetic, therapeutic and toxicological profiles of select compounds.

The compounds disclosed herein are irreversible EGFR-TKIs. The substitution locations are selected with the specific objective to impact pharmacokinetic, therapeutic, and toxicological properties of the molecule. The resulting compounds have pre-determined deuterium substitutions and exhibit more desirable profiles in terms of safety, efficacy and tolerability in the treatment of cancer (e.g., NSCLC).

In one aspect, the invention generally relates to a compound having the structural formula of:

(I)

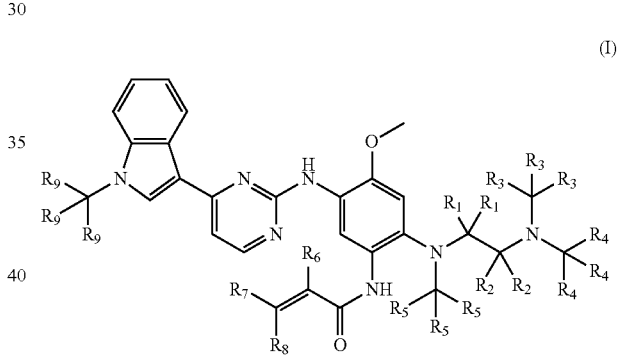

wherein each of $R_1$, $R_2$, $R_3$, $R_4$, $R_5$, $R_6$, $R_7$, $R_8$ and $R_9$ is independently selected from H and D, and at least one of $R_1$, $R_2$, $R_3$, $R_4$, $R_5$, $R_6$, $R_7$, $R_8$ and $R_9$ is D, or a pharmaceutically acceptable form thereof.

In another aspect, the invention generally relates to a pharmaceutical composition comprising a compound having the structural formula of:

(I)

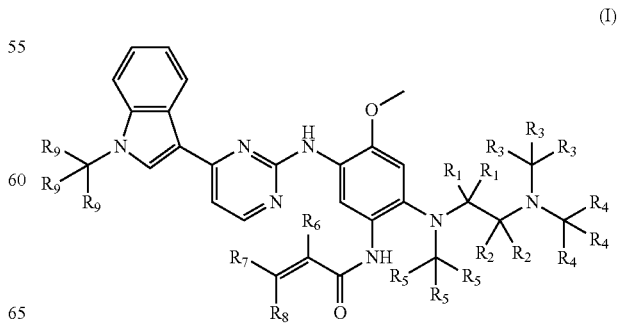

wherein each of $R_1$, $R_2$, $R_3$, $R_4$, $R_5$, $R_6$, $R_7$, $R_8$ and $R_9$ is independently selected from H and D, and at least one of $R_1$, $R_2$, $R_3$, $R_4$, $R_5$, $R_6$, $R_7$, $R_8$ and $R_9$ is D, or a pharmaceutically acceptable form thereof, effective to treat cancer (e.g., lung cancer, NSCLC), or a related disease or disorder thereof, in a mammal, including a human, and a pharmaceutically acceptable excipient, carrier, or diluent.

In yet another aspect, the invention generally relates to a unit dosage form comprising the pharmaceutical composition disclosed herein. The unit dosage form is suitable for administration to a subject suffering cancer (e.g., lung cancer, NSCLC) or a related disease and condition.

In yet another aspect, the invention generally relates to a method for treating cancer. The method includes: administering to a subject in need thereof a pharmaceutical composition comprising compound having the formula of:

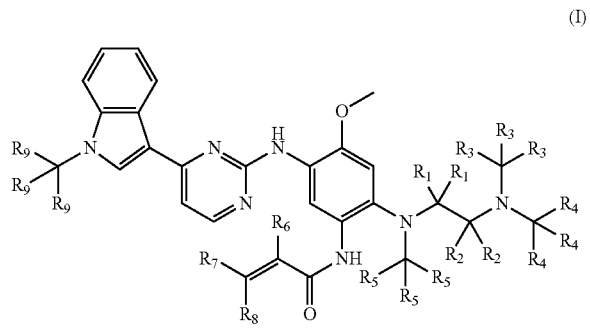

(I)

wherein each of $R_1$, $R_2$, $R_3$, $R_4$, $R_5$, $R_6$, $R_7$, $R_8$ and $R_9$ is independently selected from H and D, and at least one of $R_1$, $R_2$, $R_3$, $R_4$, $R_5$, $R_6$, $R_7$, $R_8$ and $R_9$ is D, or a pharmaceutically acceptable form thereof.

In certain embodiments, the cancer is lung cancer. In certain preferred embodiments, the cancer is non-small cell lung cancer. In certain preferred embodiments, the cancer is non-small cell lung cancer with EGFR T790M mutation.

In certain preferred embodiments, the method of treatment includes administering to a subject in need thereof a pharmaceutical composition comprising compound having the formula of:

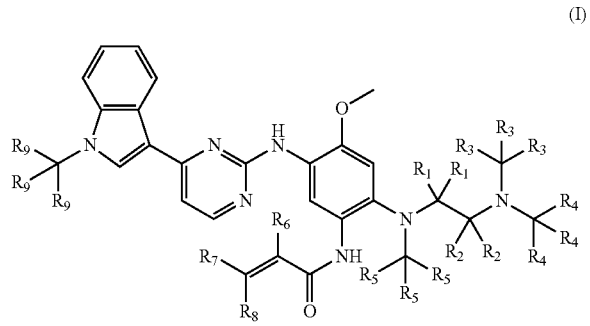

(I)

wherein each of $R_1$, $R_2$, $R_3$, $R_4$, $R_5$, $R_6$, $R_7$, $R_8$ and $R_9$ is independently selected from H and D, and at least one of $R_1$, $R_2$, $R_3$, $R_4$, $R_5$, $R_6$, $R_7$, $R_8$ and $R_9$ is D, or a pharmaceutically acceptable form thereof, in combination with one or more other anticancer agents.

BRIEF DESCRIPTION OF THE DRAWINGS

FIG. 1 shows exemplary MS spectrum of compound 9a.
FIG. 2 shows exemplary $^1$H NMR spectrum of compound 9a.

DEFINITIONS

Figure 1:
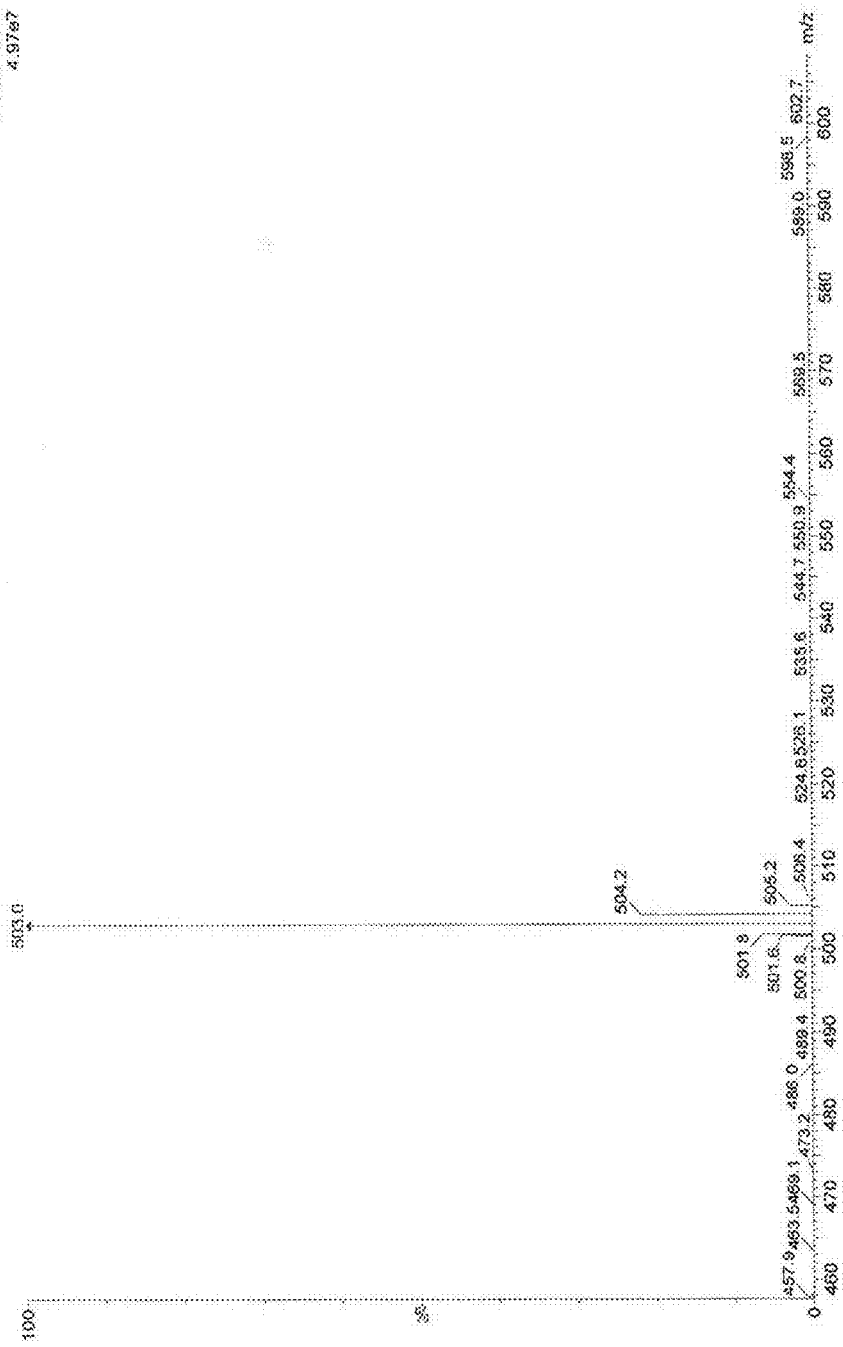

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

As used herein, "administration" of a disclosed compound encompasses the delivery to a subject of a compound as described herein, or a prodrug or other pharmaceutically acceptable derivative thereof, using any suitable formulation or route of administration, as discussed herein.

As used herein, the terms "effective amount" or "therapeutically effective amount" refer to that amount of a compound or pharmaceutical composition described herein that is sufficient to effect the intended application including, but not limited to, disease treatment, as illustrated below. In some embodiments, the amount is that effective for detectable killing or inhibition of the growth or spread of cancer cells; the size or number of tumors; or other measure of the level, stage, progression or severity of the cancer. The therapeutically effective amount can vary depending upon the intended application, or the subject and disease condition being treated, e.g., the desired biological endpoint, the pharmacokinetics of the compound, the disease being treated, the mode of administration, and the weight and age of the patient, which can readily be determined by one of ordinary skill in the art. The term also applies to a dose that will induce a particular response in target cells, e.g., reduction of cell migration. The specific dose will vary depending on, for example, the particular compounds chosen, the species of subject and their age/existing health conditions or risk for health conditions, the dosing regimen to be followed, the severity of the disease, whether it is administered in combination with other agents, timing of administration, the tissue to which it is administered, and the physical delivery system in which it is carried.

As used herein, the terms "treatment" or "treating" a disease or disorder refers to a method of reducing, delaying or ameliorating such a condition before or after it has occurred. Treatment may be directed at one or more effects or symptoms of a disease and/or the underlying pathology. Treatment is aimed to obtain beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compounds and/or compositions can be administered to a patient at risk of developing a particular disease, or to a patient reporting one or more of the physiological symptoms of a disease, even though a diagnosis of this disease may not have been made. The treatment can be any reduction and can be, but is not limited to, the complete ablation of the disease or the symptoms of the disease. As compared with an equivalent untreated control, such reduction or degree of prevention is at least 5%, 10%, 20%, 40%, 50%, 60%, 80%, 90%, 95%, or 100% as measured by any standard technique.

As used herein, the term "therapeutic effect" refers to a therapeutic benefit and/or a prophylactic benefit as described herein. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, the term "pharmaceutically acceptable ester" refers to esters that hydrolyze in vivo and include those that break down readily in the human body to leave the parent compound or a salt thereof. Such esters can act as a prodrug as defined herein. Pharmaceutically acceptable esters include, but are not limited to, alkyl, alkenyl, alkynyl, aryl, aralkyl, and cycloalkyl esters of acidic groups, including, but not limited to, carboxylic acids, phosphoric acids, phosphinic acids, sulfinic acids, sulfonic acids and boronic acids. Examples of esters include formates, acetates, propionates, butyrates, acrylates and ethylsuccinates. The esters can be formed with a hydroxy or carboxylic acid group of the parent compound.

As used herein, the term "pharmaceutically acceptable enol ethers" include, but are not limited to, derivatives of formula —C=C(OR) where R can be selected from alkyl, alkenyl, alkynyl, aryl, aralkyl and cycloalkyl. Pharmaceutically acceptable enol esters include, but are not limited to, derivatives of formula —C=C(OC(O)R) where R can be selected from hydrogen, alkyl, alkenyl, alkynyl, aryl, aralkyl and cycloalkyl.

As used herein, a "pharmaceutically acceptable form" of a disclosed compound includes, but is not limited to, pharmaceutically acceptable salts, hydrates, solvates, isomers, prodrugs, and isotopically labeled derivatives of disclosed compounds. In one embodiment, a "pharmaceutically acceptable form" includes, but is not limited to, pharmaceutically acceptable salts, isomers, prodrugs and isotopically labeled derivatives of disclosed compounds. In some embodiments, a "pharmaceutically acceptable form" includes, but is not limited to, pharmaceutically acceptable salts, stereoisomers, prodrugs and isotopically labeled derivatives of disclosed compounds.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a parent compound with a suitable base or acid, respectively. Pharmaceutically acceptable salts derived from appropriate bases include alkali metal, alkaline earth metal, ammonium and $N^+(C_{1-4}alkyl)^4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt can be chosen from ammonium, potassium, sodium, calcium, and magnesium salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" (or "pro-drug") refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it can enhance absorption from the digestive tract, or it can enhance drug stability for long-term storage.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

As used herein, the "low dosage" refers to at least 5% less (e.g., at least 10%, 20%, 50%, 80%, 90%, or even 95%) than the lowest standard recommended dosage of a particular compound formulated for a given route of administration for treatment of any human disease or condition. For example, a low dosage of an agent that reduces glucose levels and that is formulated for administration by inhalation will differ from a low dosage of the same agent formulated for oral administration.

As used herein, the "high dosage" is meant at least 5% (e.g., at least 10%, 20%, 50%, 100%, 200%, or even 300%) more than the highest standard recommended dosage of a particular compound for treatment of any human disease or condition.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure.

Solvates and polymorphs of the compounds of the invention are also contemplated herein. Solvates of the compounds of the present invention include, for example, hydrates.

DETAILED DESCRIPTION OF THE INVENTION

The invention provides novel chemical entities that may be used to treat cancer (e.g., NSCLC). These compounds are biochemically potent and physiologically active with improved pharmacokinetic, therapeutic and toxicological properties over N-(2-{2-dimethylaminoethyl-methylamino}-4-methoxy-5-{[4-(1-methylindol-3-yl)pyrimidin-2-yl]amino}phenyl)prop-2-enamide, shown below.

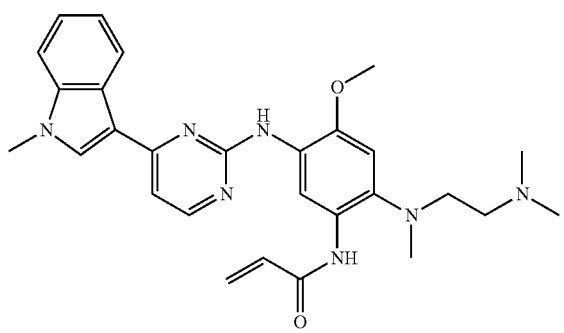

Osimertinib

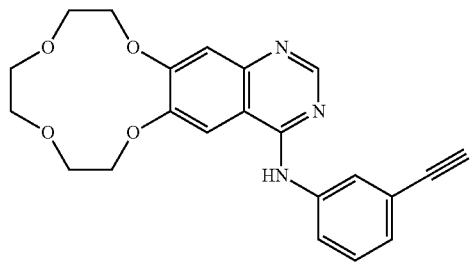

Icotinib

The compounds disclosed herein are deuterium-substituted versions of the above compound, where one or more hydrogen atoms are substituted with deuterium at strategic locations of the molecule. Such strategic deuterium substitution leads to positive impact on the pharmacokinetic, therapeutic and toxicological profiles of select compounds. The compounds disclosed herein are irreversible EGFR-TKIs. The substitution locations are selected with the specific objective to impact pharmacokinetic, therapeutic, and toxicological properties of the molecule. The resulting compounds have pre-determined deuterium substitutions and exhibit more desirable profiles in terms of safety, efficacy and tolerability in the treatment of cancer (e.g., NSCLC).

First generation reversible TKIs (e.g., erlotinib, gefitinib and icotinib) have been reported to be most effective in advanced NSCLC patients whose tumors harbor recurrent somatic activating mutations (EGFRm+). Patients with EGFRm+ tumors normally show good

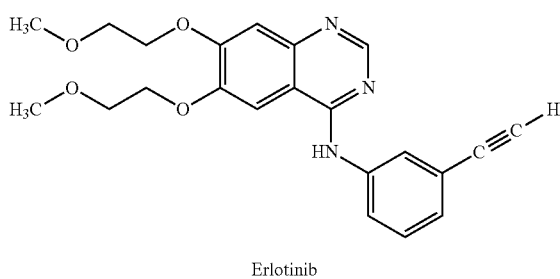

Erlotinib

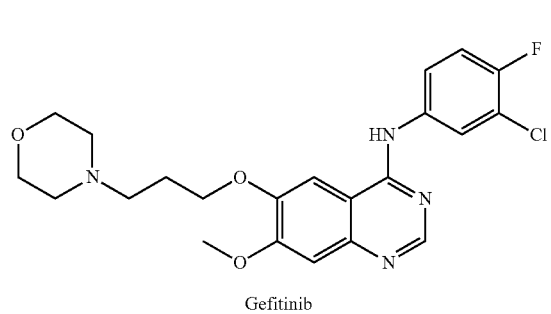

Gefitinib initial responses to the first generation TKIs. Most patients who respond to therapy, however, eventually acquire disease progression in about a year (~9 to 14 months) of treatment. Side effects have also been identified with the use of first generation TKIs, including skin rash and diarrhea reportedly due to the inhibition of wild-type EGFR in skin and gastrointestinal organs. (Pao, et al. 2010 *Nature Reviews Cancer* 10:760-74; Maemondo, et al. 2010 *The New England Journal of Medicine* 362:2380-8; Mitsudomi, et al. 2009 *The Lancet Oncology* 11:121-8; Mok, et al. 2009 *The New England Journal of Medicine* 361:947-57; Rosell, et al. 2012 *The Lancet Oncology;* 13:239-46; Zhou, et al. 2011 *The Lancet Oncology* 12:735-42; Burtness, et al. 2009 *JNCCN* Vol. 7. Suppl 1, p. 55-21.quiz S2-4.)

Acquisition of a second mutation in EGFR (T790M) is the most common resistance mechanism that is detected in >50% of patients after disease progression. The T790M mutation is believed to cause the receptor refractory to inhibition by the first generation EGFR TKIs through exerting effects on both steric hindrance and increased ATP affinity. (Kobayashi, et al. 2005 *New England Journal of Medicine* 352:786-92; Pao, et al. 2005 *PLoS Medicine* 2:e73; Sos, et al. 2010 *Cancer Research* 70:868-74; Yun, et al. 2008 *Proceedings of the National Academy of Sciences USA.;* 105:2070-5.)

Second generation irreversible EGFR TKIs (e.g., neratinib, afatinib and dacomitinib) are effective in untreated EGFR mutant lung cancer. They have failed, however, to effectively

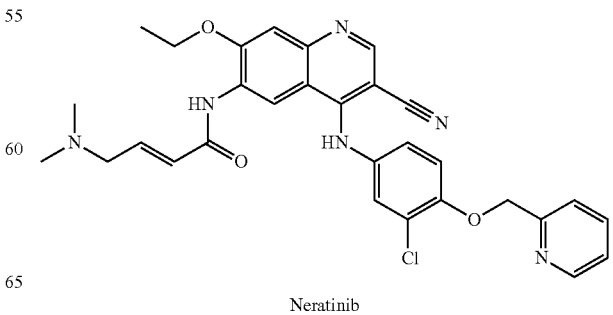

Neratinib

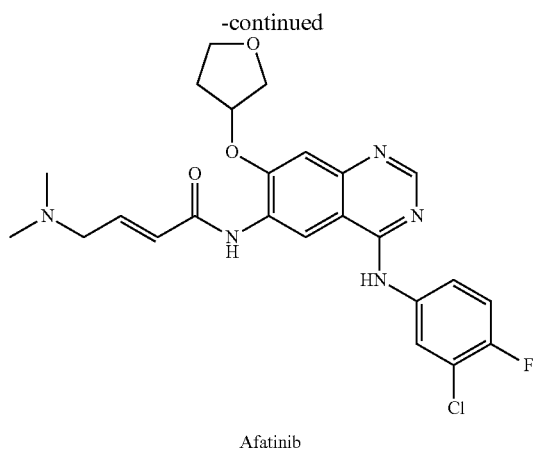

Afatinib

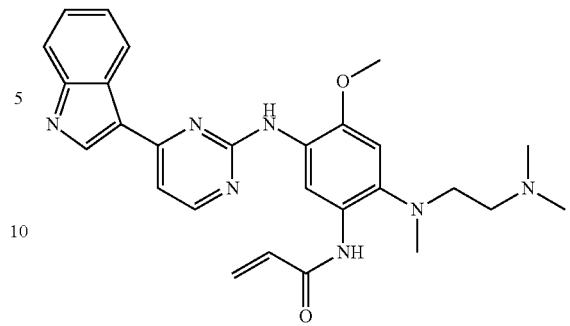

Demethylated metabolite (M1) of osimertinib

Another compound, shown below (AZ7550), has reportedly displayed similar mutant EGFR selectivity but has a low affinity towards wild-type EGFR.

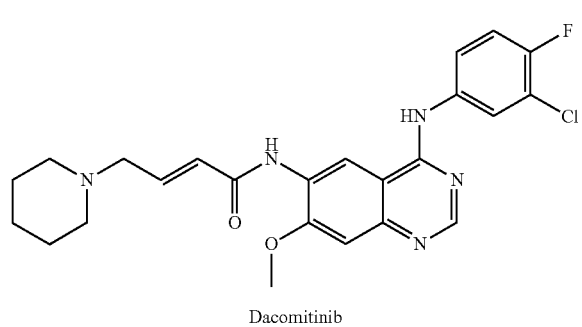

Dacomitinib

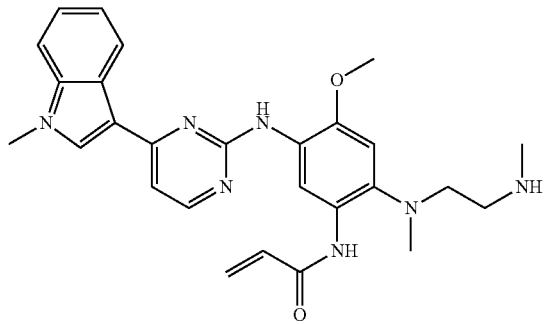

AZ7550 address T790M-mediated resistance. This is in part because of their dose-limiting toxicity connected to the non-selective inhibition of wild-type EGFR. (Li, et al. 2008 *Oncogene* 27:4702-11; Engelman, et al. 2007 *Cancer Research* 67:11924-32; Ramalingam, et al. 2012 *J Clin Oncol* 30:3337-44; Sequist, et al. 2013 *J Clin Oncol* 31:3327-3334; Miller, et al. 2012 *The Lancet Oncology* 13:528-38; Katakami, et al. 2013 *J Clin Oncol* 31:3335-3341; Eskens, et al. 2008 *British Journal of Cancer* 98:80-5.)

Therefore, targeted therapeutics against acquired resistance are quite limited. A significant unmet need exists for EGFR TKIs that can effectively target T790M tumors with little or no activity towards wild-type EGFR.

Osimertinib has been shown to be potent to mutant EGFR; however, a demethylated metabolite of osimertinib shows a similar affinity towards wild-type EGFR. Thus, de-methylation at the indole position of osimertinib gives rise to a toxic metabolite, which has a higher affinity to wild-type EGFR and causes serious side effects during treatment. Such high affinity to wild-type EGFR raises serious safety issues and significantly limits the overall effectiveness of osimertinib in treating cancer patients. Furthermore, the metabolite also increases IGF1R potency that may lead to hyperglycemia in human treatment.

The kinetic isotope effect (KIE) is the change in the rate of a chemical reaction when one of the atoms in the reactants is substituted with one of its isotopes. A primary kinetic isotope effect may be found when a bond to the isotopically labeled atom is being formed or broken. A secondary kinetic isotope effect is observed when no bond to the isotopically substituted atom in the reactant is broken or formed in the rate-determining step of a reaction. Deuterium kinetic isotope effect (DKIE) is the kinetic isotope effect present in the case of a C—H bond when $^1$H is replaced with deuterium (D or $^2$H), which is a stable and non-radioactive isotope of $^1$H with twice its mass. DKIE results from the greater amount of energy required to break a C-D bond versus a C—$^1$H bond.

While deuteration of drugs to improve pharmacokinetics, pharmacodynamics, or toxicity properties has been attempted with certain classes of drugs, in many cases the mechanism of action of a drug may remain unclear or the effect of deuteration unpredictable. For a compound of many potential candidates for study of DKIE, synthetic difficulties can be challenging as well. Thus, strategically selected deuterium replacement can be not only difficult from a synthetic perspective, it is physiologically and biochemically unpredictable as well. One key feature of the present invention is the strategically selective deuteration of osimertinib with the aim to reduce toxicity via blocking the metabolic process that would result in the formation of toxic metabolites. Deuteration of the methyl group at the indole position, as disclosed herein, significantly restrains the metabolic pathway of demethylation and ultimately improves toxicological property of the molecule.

Another key feature of the present invention is the strategically selective deuteration of osimertinib with the aim to impact reactivity of the molecule via deuteration at the ethenyl group to influence the binding and distribution properties of the molecule.

Without wishing to be bound by the theory, the compounds of the invention bind to the EGFR kinase irreversibly by targeting the cysteine-797 residue in the ATP binding site via covalent bond formation. The acrylamide moiety of the molecule serves as a chemically reactive Michael Acceptor (MA) electrophilic "warhead" which reacts with cysteine nucleophile. The ensuing 1,4-conjugate addition reaction of these inactivators results in an irreversible covalent adduct. Studies have indicated that the reactivity of forming covalent bonding contribute to the overall cellular inhibition of EGFR-L858R/T790M as well as the capability of non-covalent reversible binding. The improvement of reactivity of the warhead moiety can ultimately increase efficacy in human treatment. While the reactivity of covalent inhibitors with cysteine nucleophile of EGFR shown to be essential to both biochemical and cell potencies, specific cysteine oxidation has been identified here as a possible drug resistance mechanism. Literatures show that EGFR-Cys797 oxidation (—SH, unoxidized, —SO2H sulfinylated, —SSG, glutathiolated) can profoundly affect inhibitor affinity. It is considered as a mechanism that causes drug resistance. Schwaitz, et al. 2014 *PNAS* 111:173-178; Ward, et al. 2013 *J. Med. Chem.* 56, 7025-7048; Engel, et al. 2015 *ACS Med. Chem. Lett.* 7: 2-5; Krishnan, et al. 2014 *J. Am. Chem. Soc.* 136, 12624-12630. Thus, enhancing the reactivity of the warhead and decreasing the steric hindrance may overcome the drug resistance to certain extent.

Based on above reasons and other considerations, optimizing reactivity of the warhead while increasing or maintaining the non-covalent binding capability of a compound is an approach to improve efficacy and reduce toxicity.

Together, these two features synergistically lead to overall improvements in pharmacokinetic, therapeutic, and toxicological properties by the disclosed compounds.

Compared to osimertinib, compounds disclosed herein are potent, selective and irreversible (covalent) inhibitors of both EGFR sensitizing and T790M resistance mutations with much less activity towards wild-type EGFR. Compounds of the invention inhibit phosphorylation of mutant-EGFR much more potently than against wild-type EGFR. Compounds of the invention are also better tolerated and give rise to lesser side effects because of the high selectivity and much reduced activity towards wild-type EGFR. Furthermore, the compounds of the invention have better pharmacological properties, such as solubility, permeability, lower plasma binding ratio and/or tumor penetration.

In addition to use as a third-line therapy, compounds of the invention may also be used to treat EGFRm+ TKI-naïve patients by targeting both sensitizing and T790M tumour cell populations that co-exist in a proportion of tumors. This approach may lead to delayed disease progression and improved survival rate.

In one aspect, the invention generally relates to a compound having the structural formula of:

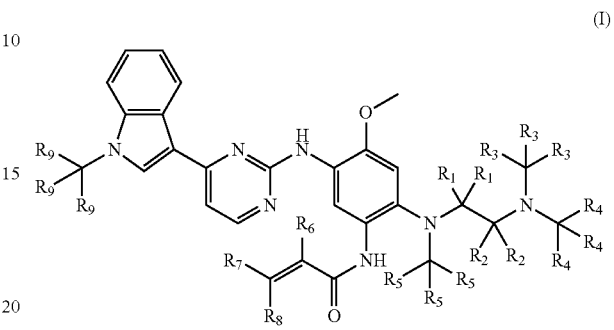

(I)

wherein each of $R_1$, $R_2$, $R_3$, $R_4$, $R_5$, $R_6$, $R_7$, $R_8$ and $R_9$ is independently selected from H and D, and at least one of $R_1$, $R_2$, $R_3$, $R_4$, $R_5$, $R_6$, $R_7$, $R_8$ and $R_9$ is D, or a pharmaceutically acceptable form thereof.

In certain embodiments of (I), each of $R_9$ is D and the compound has the following structure:

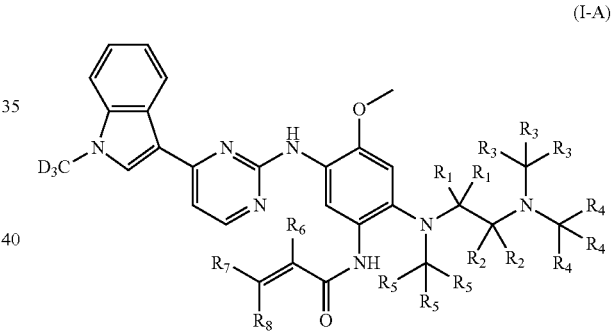

(I-A)

wherein each of $R_1$, $R_2$, $R_3$, $R_4$, $R_5$, $R_6$, $R_7$ and $R_8$ is independently selected from H and D.

In certain embodiments of (I), each of $R_6$, $R_7$ and $R_8$ is D and the compound has the following structure:

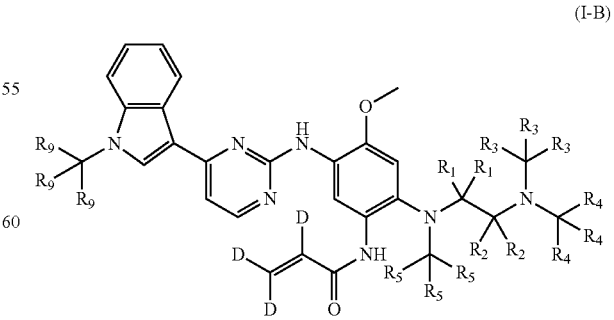

(I-B)

wherein each of $R_1$, $R_2$, $R_3$, $R_4$, $R_5$ and $R_9$ is independently selected from H and D.

In certain embodiments of (I), each of $R_1$, $R_2$, $R_3$, $R_4$ and $R_5$ is D and the compound has the following structure:

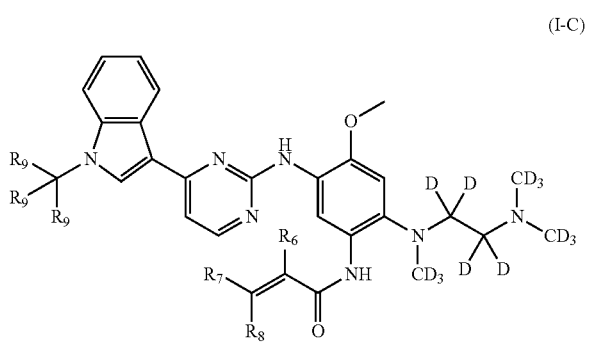

(I-C)

wherein each of $R_6$, $R_7$, $R_8$ and $R_9$ is independently selected from H and D.

In certain embodiments of (I-A), each of $R_6$, $R_7$ and $R_8$ is D, having the following structural formula,

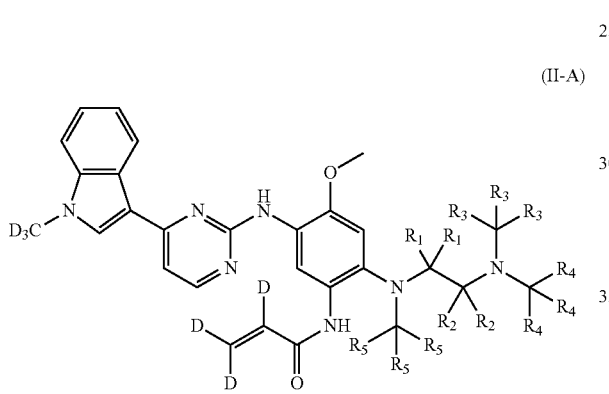

(II-A)

with each of $R_1$, $R_2$, $R_3$, $R_4$ and $R_5$ is independently selected from H and D.

In certain embodiments of (II-A), each of $R_1$, $R_2$, $R_3$, $R_4$ and $R_5$ is H.

In certain embodiments of (I-A), each of $R_1$, $R_2$, $R_3$, $R_4$ and $R_5$ is D, having the following structural formula,

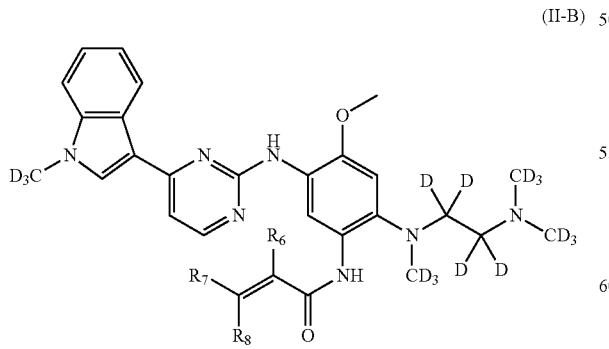

(II-B)

In certain embodiments of (II-B), each of $R_6$, $R_7$ and $R_8$ is H.

In certain embodiments of (I-B), each of $R_1$, $R_2$, $R_3$, $R_4$ and $R_5$ is D, having the following structural formula,

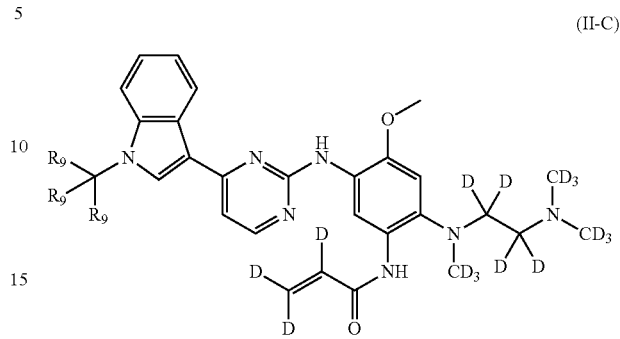

(II-C)

In certain embodiments of (II-C), each of $R_9$ is H.

In certain embodiments of (II-C), each of $R_9$ is D, having the following structural formula,

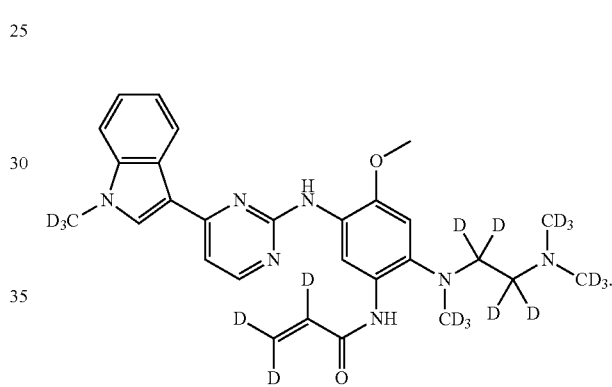

In certain embodiments of (I-A), each of $R_1$ and $R_2$ is D and each of $R_6$, $R_7$ and $R_8$ is D, having the following structural formula,

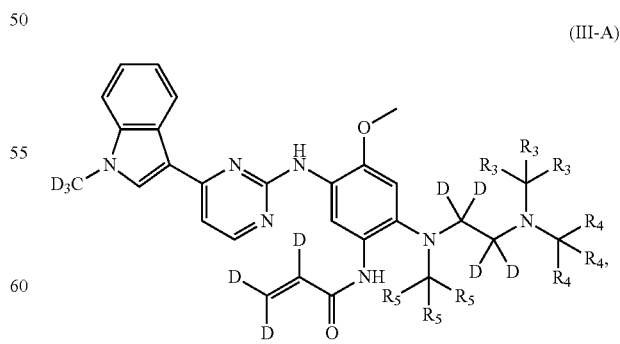

(III-A)

with the other R's as first defined above.

Examples of Formula (III-A)
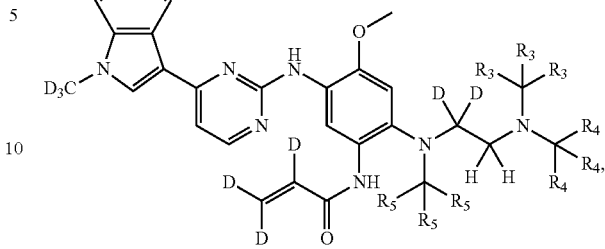
(III-B)
with the other R's as first defined above.
Examples of Formula (III-B)
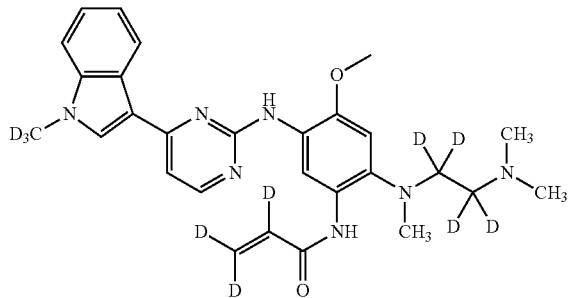 [SMILES: [2H]C([2H])=C([2H])C(=O)Nc1cc(Nc2nccc(-c3cn(C([2H])([2H])[2H])c4ccccc34)n2)c(OC)cc1N(C([2H])([2H])[2H])C([2H])([2H])C([2H])([2H])N(C([2H])([2H])[2H])C([2H])([2H])[2H]]
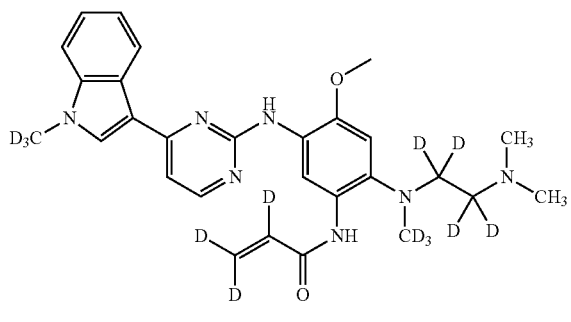
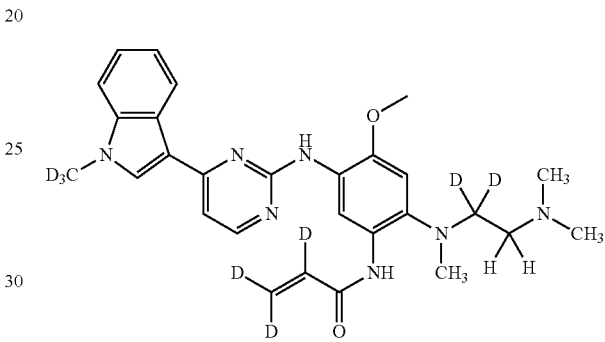
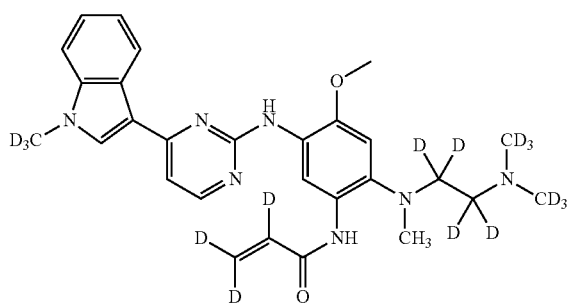
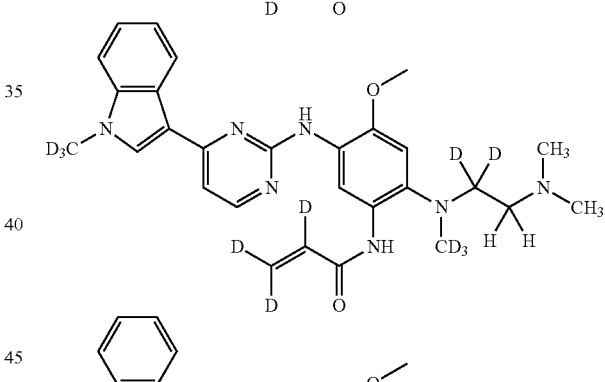
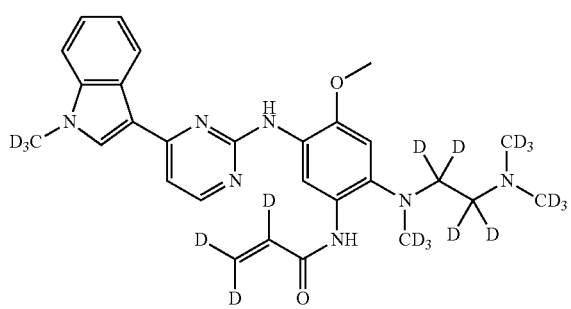
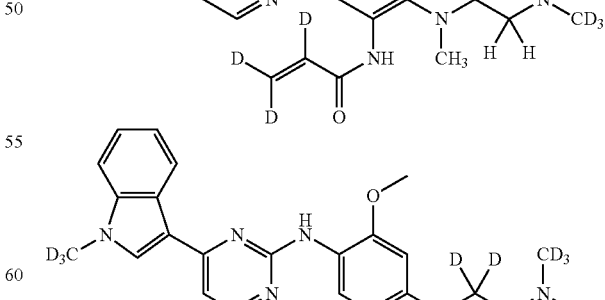
In certain embodiments of (I-A), each $R_1$ is D, each $R_2$ is H, and each of $R_6$, $R_7$ and $R_8$ is D, having the following structural formula, In certain embodiments of (I-A), each $R_1$ is H, each $R_2$ is D, and each of $R_6$, $R_7$ and $R_8$ is D, having the following structural formula, (III-C)

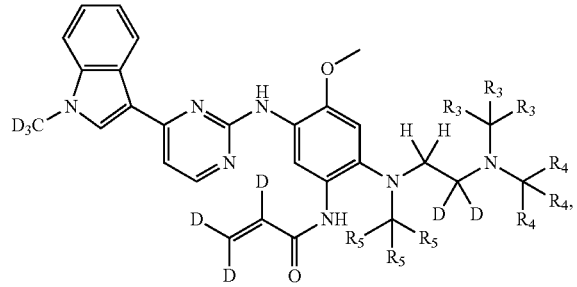

with the other R's as first defined above.

Examples of Formula (III-C)

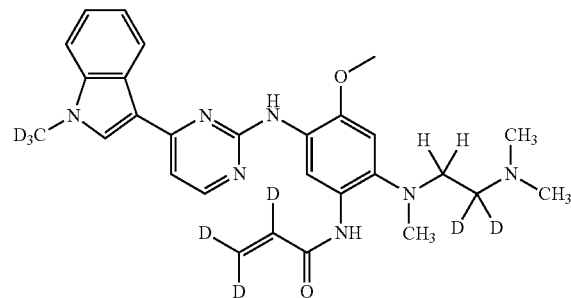 [SMILES: [2H]C([2H])=C([2H])C(=O)Nc1cc(Nc2nccc(-c3cn(C([2H])([2H])[2H])c4ccccc34)n2)c(OC)cc1N(C([2H])([2H])[2H])C([2H])([2H])C([2H])([2H])N(C([2H])([2H])[2H])C([2H])([2H])[2H]]

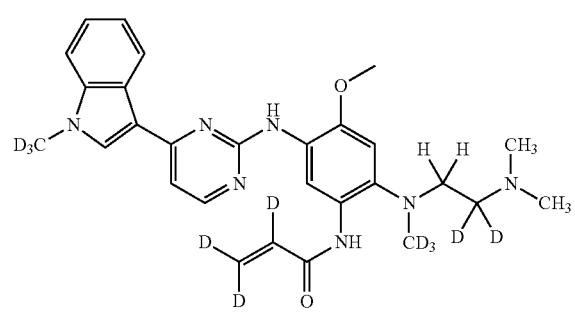

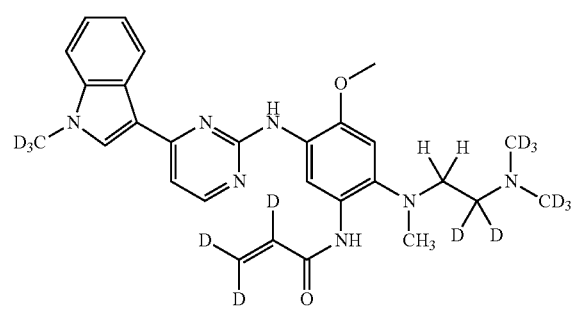 [SMILES: [2H]C([2H])=C([2H])C(=O)Nc1cc(Nc2nccc(-c3cn(C([2H])([2H])[2H])c4ccccc34)n2)c(OC)cc1N(C([2H])([2H])[2H])C([2H])([2H])C([2H])([2H])N(C([2H])([2H])[2H])C([2H])([2H])[2H]]

-continued

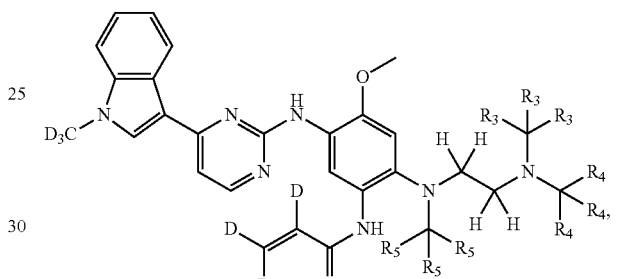

In certain embodiments of (I-A), each of $R_1$ and $R_2$ is H, and each of $R_6$, $R_7$ and $R_8$ is D, at least one of $R_3$, $R_4$ and $R_5$ is D, having the following structural formula, (III-D)

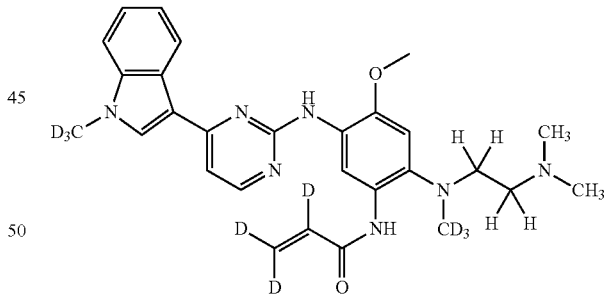

with the other R's as first defined above.

Examples of Formula (III-D)

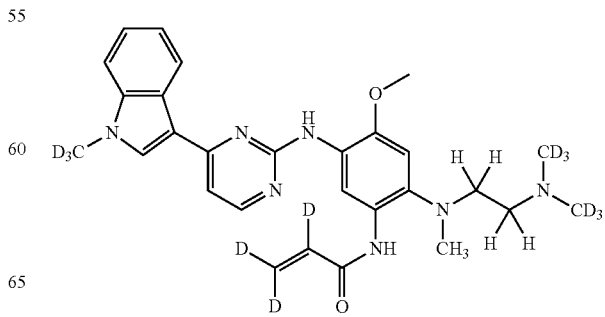

-continued

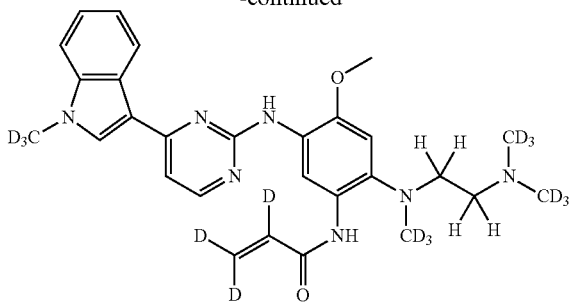

Any suitable salts may be employed. In certain preferred embodiments, the compounds of the invention are in the form of a mesylate salt.

In another aspect, the invention generally relates to a pharmaceutical composition comprising a compound having the structural formula of:

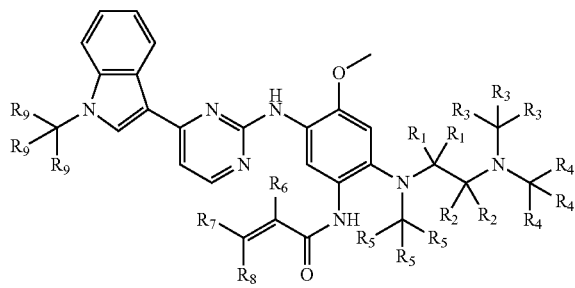

(I)

wherein each of $R_1$, $R_2$, $R_3$, $R_4$, $R_5$, $R_6$, $R_7$, $R_8$ and $R_9$ is independently selected from H and D, and at least one of $R_1$, $R_2$, $R_3$, $R_4$, $R_5$, $R_6$, $R_7$, $R_8$ and $R_9$ is D, or a pharmaceutically acceptable form thereof, effective to treat cancer (e.g., lung cancer, NSCLC), or a related disease or disorder thereof, in a mammal, including a human, and a pharmaceutically acceptable excipient, carrier, or diluent.

In yet another aspect, the invention generally relates to a unit dosage form comprising the pharmaceutical composition disclosed herein. The unit dosage is suitable for administration to a subject suffering cancer (e.g., lung cancer, NSCLC) or a related disease and condition.

In yet another aspect, the invention generally relates to a method for treating cancer or a disease or disorder. The method includes: administering to a subject in need thereof a pharmaceutical composition comprising compound having the formula of:

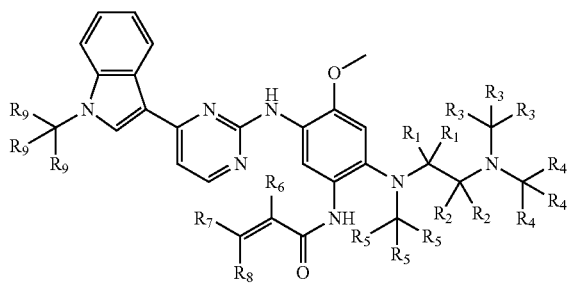

(I)

wherein each of $R_1$, $R_2$, $R_3$, $R_4$, $R_5$, $R_6$, $R_7$, $R_8$ and $R_9$ is independently selected from H and D, and at least one of $R_1$, $R_2$, $R_3$, $R_4$, $R_5$, $R_6$, $R_7$, $R_8$ and $R_9$ is D, or a pharmaceutically acceptable form thereof.

In certain embodiments, the cancer is lung cancer. In certain preferred embodiments, the cancer is non-small cell lung cancer. In certain preferred embodiments, the cancer is non-small cell lung cancer with EGFR T790M mutation.

In certain embodiments, the pharmaceutical composition of the invention is administered as a last line cancer therapeutic. In certain embodiments, the pharmaceutical composition is administered as a second line cancer therapeutic. In certain embodiments, the pharmaceutical composition is administered as a first line cancer therapeutic.

In certain embodiments of the method, the pharmaceutical composition is administered to a subject is a NSCLC patient with EGFRm+ and EGFR T790M mutation. In certain embodiments, the subject has been previously treated with one or more first generation reversible TKIs. In certain embodiments, the subject has been previously treated with one or more second generation irreversible TKIs. In certain embodiments, the subject has been previously treated with both one or more first generation TKIs and one or more of second generation irreversible TKIs.

In certain embodiments, the diseases and conditions that may benefit from treatment using the compounds, pharmaceutical composition, unit dosage form and treatment method disclosed herein include any diseases and disorders that may be addressed by EGFR-TKIs.

In certain preferred embodiments, the method of treatment includes administering to a subject in need thereof a pharmaceutical composition comprising compound having the formula of:

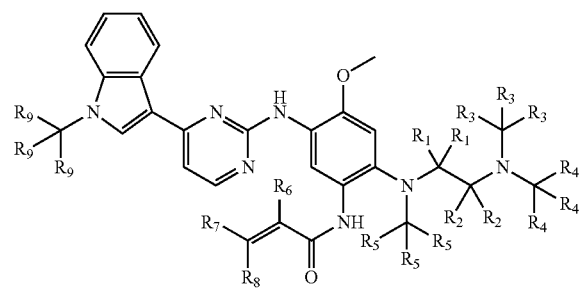

(I)

wherein each of $R_1$, $R_2$, $R_3$, $R_4$, $R_5$, $R_6$, $R_7$, $R_8$ and $R_9$ is independently selected from H and D, and at least one of $R_1$, $R_2$, $R_3$, $R_4$, $R_5$, $R_6$, $R_7$, $R_8$ and $R_9$ is D, or a pharmaceutically acceptable form thereof, in combination with one or more other anticancer agents.

In certain preferred embodiments, the one or more other anticancer agents are selected from methotrexate, afatinib dimaleate, alectinib, pemetrexed disodium, bevacizumab, carboplatin, ceritinib, crizotinib, ramucirumab, docetaxel, erlotinib hydrochloride, methotrexate, gefitinib, gemcitabine hydrochloride, pembrolizumab, mechlorethamine hydrochloride, vinorelbine tartrate, necitumumab, nivolumab, paclitaxel, and erlotinib hydrochloride.

Any appropriate route of administration can be employed, for example, parenteral, intravenous, subcutaneous, intramuscular, intraventricular, intracorporeal, intraperitoneal, rectal, or oral administration. Most suitable means of administration for a particular patient will depend on the nature and severity of the disease or condition being treated or the nature of the therapy being used and on the nature of the active compound.

Solid dosage forms for oral administration include capsules, tablets, pills, powders, and granules. In such solid dosage forms, the compounds described herein or derivatives thereof are admixed with at least one inert customary excipient (or carrier) such as sodium citrate or dicalcium phosphate or (i) fillers or extenders, as for example, starches, lactose, sucrose, glucose, mannitol, and silicic acid, (ii) binders, as for example, carboxymethylcellulose, alignates, gelatin, polyvinylpyrrolidone, sucrose, and acacia, (iii) humectants, as for example, glycerol, (iv) disintegrating agents, as for example, agar-agar, calcium carbonate, potato or tapioca starch, alginic acid, certain complex silicates, and sodium carbonate, (v) solution retarders, as for example, paraffin, (vi) absorption accelerators, as for example, quaternary ammonium compounds, (vii) wetting agents, as for example, cetyl alcohol, and glycerol monostearate, (viii) adsorbents, as for example, kaolin and bentonite, and (ix) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others known in the art.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like. Besides such inert diluents, the composition can also include additional agents, such as wetting, emulsifying, suspending, sweetening, flavoring, or perfuming agents.

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

EXAMPLES

Compound Syntheses

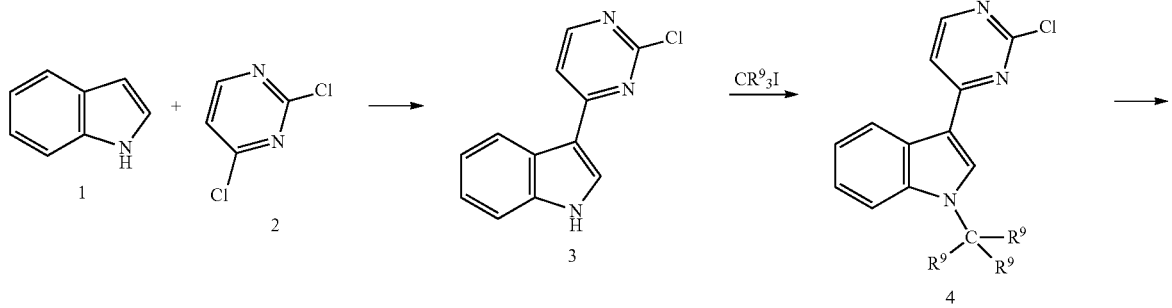

Scheme 1

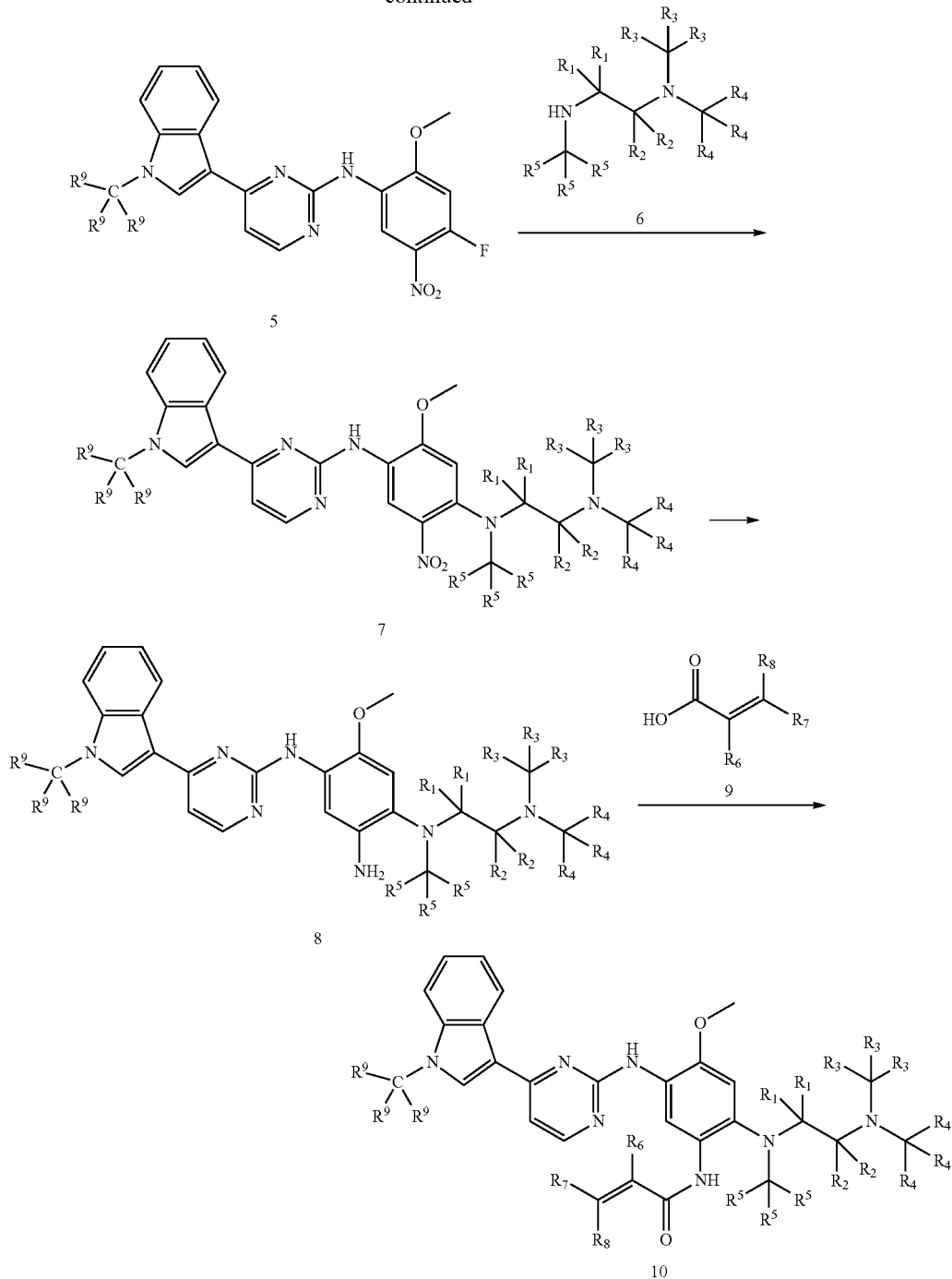

Synthetic Procedure:
Step 1
3-(2-Chloropyrimidin-4-yl)-1H-indole (compound 3). Methylmagnesium bromide (3 M in diethyl ether) (100 mL) was added dropwise over a period of 10 min to a stirred solution of 1H-indole (35.2 g) in THF (500 mL) at 0° C. under nitrogen. The resulting solution was stirred for 60 min. 2,4-Dichloropyrimidine (44.7 g) was added in one portion. The resulting solution was heated at reflux for 5 hours and stirred at ambient temperature for 16 h. The reaction was quenched by the addition of water (400 mL) and EtOAc (500 mL). The organic layer was evaporated to dryness and purified by flash silica chromatography. Pure fractions were evaporated to dryness. 3-(2-chloropyrimidin-4-yl)-1H-indole (compound 3, 19 g) as a yellow solid.

Step 2
3-(2-Chloropyrimidin-4-yl)-1-methylindole (compound 4). Sodium hydride (2.7 g, 60% in mineral oil) was added portionwise to 3-(2-chloropyrimidin-4-yl)-1H-indole (12 g) in THF (250 mL) at 0° C. The resulting mixture was stirred at 0° C. for 30 min before $CR^9_3I$ (1.3 equiv.) was added. The mixture was stirred at 0° C. for 1 h. The reaction was quenched by the addition of saturated aqueous NaHCO₃ solution (400 mL) and EtOAc (400 mL). The organic layer was washed with saturated brine (200 mL). The organic layer was evaporated to afford crude product (compound 4, 9.3 g) as a pale orange solid.

Step 3

N-(4-Fluoro-2-methoxy-5-nitrophenyl)-4-(1-methylindol-3-yl)-pyrimidin-2-amine (compound 5). 4-Methylbenzenesulfonic acid hydrate (8.7 g) was added in one portion to 3-(2-chloropyrimidin-4-yl)-1-methylindole (9.3 g) and 4-fluoro-2-methoxy-5-nitroaniline (7.1 g) in n-butanol (200 mL). The resulting mixture was stirred at reflux for 1 h. The mixture was cooled to room temperature. The precipitate was collected by filtration, washed with n-butanol (50 mL), and dried under vacuum to afford N-(4-fluoro-2-methoxy-5-nitrophenyl)-4-(1-methylindol-3-yl)pyrimidin-2-amine as a yellow solid (Compound 5, 15.5 g).

Step 4

N'-(2-Dimethylaminoethyl)-2-methoxy-N'-methyl-N-[4-(1-methylindol-3-yl)pyrimidin-2-yl]-5-nitrobenzene-1,4-diamine (Compound 7). Compound 6 (7.7 mL) was added to a suspension of N-(4-fluoro-2-methoxy-5-nitrophenyl)-4-(1-methylindol-3-yl)pyrimidin-2-amine (compound 5, 15.5 g, 0.79) and K2CO3 (16.3 g) in DMF (60 mL). The mixture was heated at 60° C. for 60 min and then water (150 mL) was added. Solids were filtered and rinsed with water. The crude dark red product was directly used in the next step without further purification.

Step 5

N1-(2-Dimethylaminoethyl)-5-methoxy-N1-methyl-N4-[4-(1-methylindol-3-yl)pyrimidin-2-yl]benzene-1,2,4-triamine (Compound 8). Compound 7 from the previous step, iron (12.8 g), and ammonium chloride (1.42 g) were heated in ethanol (100 mL) and water (30 mL) at reflux for 1.5 h. The mixture was cooled and filtered. The solids were rinsed with DCM. The filtrate was concentrated to approximately 20 mL and NaOH (1 N, 50 mL) was added. The gray precipitates were filtered off and rinsed with DCM. The mixture was partitioned and the organic layer was washed with NH4OH (50 mL), brine (100 mL) and concentrated to a brown foam (compound 8, 12 g).

Step 6

Compound 10. Compound 9 (0.32 g) was added dropwise to a stirred solution of compound 8 (2 g), EDC-HCl (1.28 g) and DIPEA (1.15 g) in DMF (10 mL). The mixture was stirred for 16 hours and then diluted with DCM (50 mL) and washed with brine, NH4OH, brine. The organic layer was concentrated and purified by column chromatography. Pure fractions were evaporated to dryness and triturated with ether to afford compound 10 (0.35 g) as an off-white solid.

Compound 9a, $R_1=R_2=R_3=R_4=R_5=H$, $R_6=R_7=R_8=D$, $R_9=H$ (D3-Osimertinib)

Mass Spec: $[M+H]^+=503.3$. ¹H-NMR (300 MHz, DMSO-$d_6$): 10.16 (s, 1H), 9.85 (s, 1H), 9.06 (s, 1H), 8.36 (d, 1H), 8.06 (m, 1H), 7.72 (s, 1H), 7.36 (m, 1H), 7.27-7.18 (m, 3H), 6.77 (s, 1H), 3.96 (s, 3H), 3.85 (s, 3H), 2.87 (s, 2H), 2.67 (s, 3H), 2.25 (b, 8H); HPLC: 96.1% (AUC, 254 nm).

Figure 2:
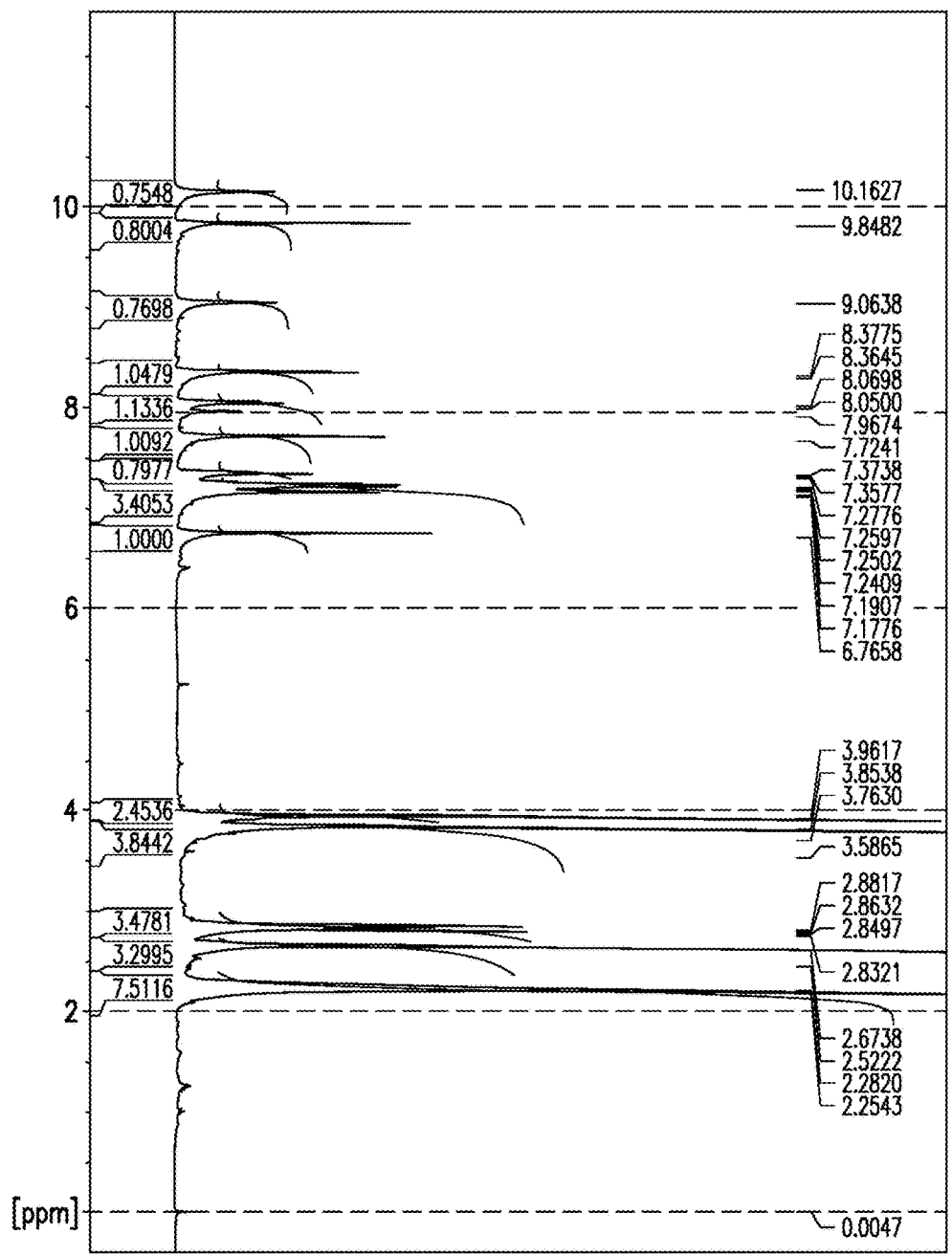

FIG. 1 shows the MS spectrum of compound 9a.
FIG. 2 shows ¹H NMR spectrum of compound 9a.

Compound 9b, $R_1=R_2=R_3=R_4=R_5=H$, $R_6=R_7=R_8=R_9=D$ (D6-Osimertinib)

Mass Spec: $[M+H]^+=506.1$. ¹H-NMR (300 MHz, DMSO-$d_6$): 10.18 (s, 1H), 9.13 (s, 1H), 8.67 (s, 1H), 8.32 (m, 1H), 8.23 (m, 1H), 7.89 (s, 1H), 7.51 (m, 1H), 7.22 (m, 2H), 7.15 (m, 1H), 7.03 (s, 1H), 3.85 (s, 3H), 2.88 (b, 2H), 2.71 (s, 3H), 2.30 (b, 2H), 2.21 (b, 6H); HPLC: 97.0%, (AUC 254 nm)

Figure 3:
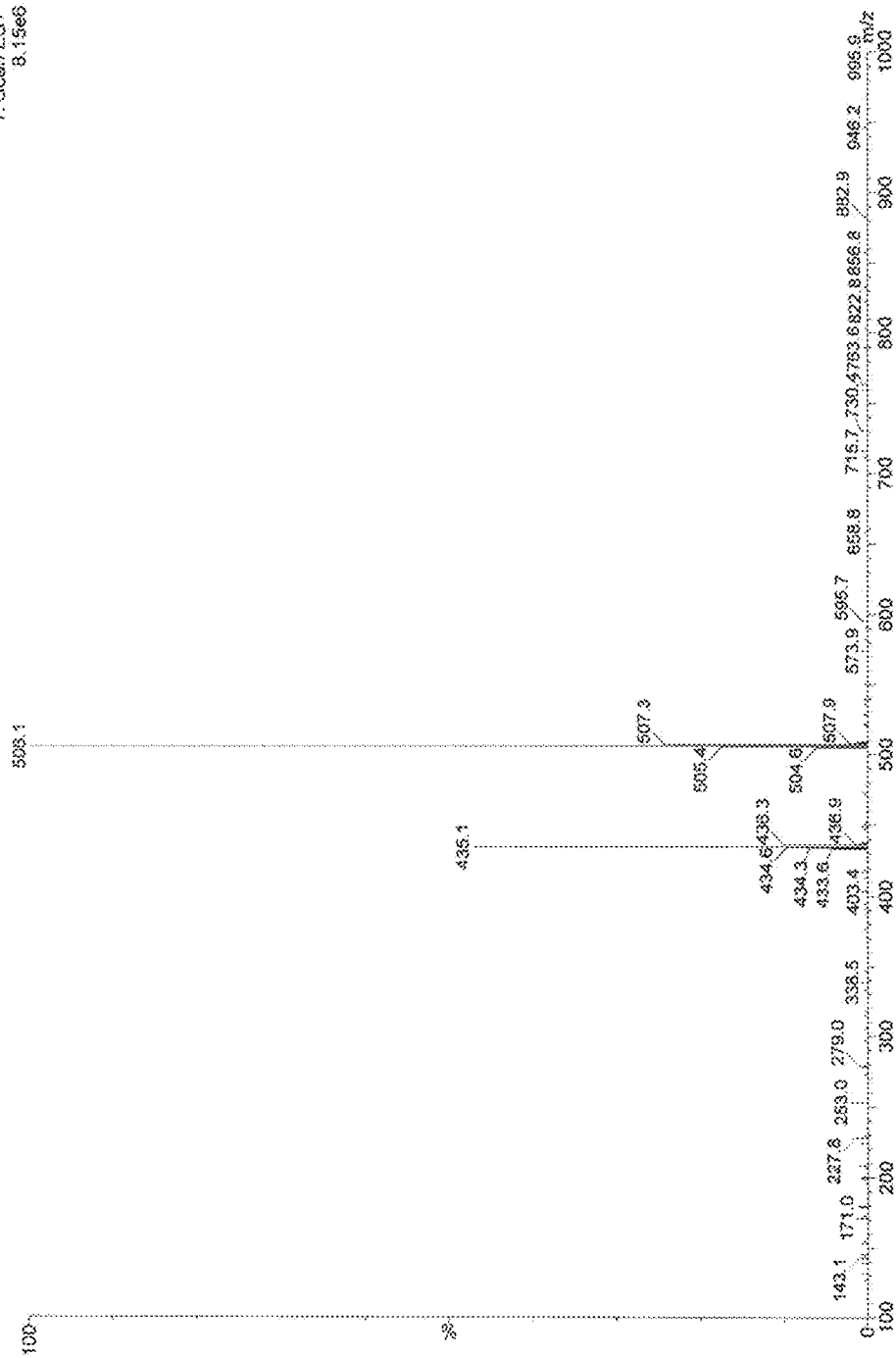
FIG. 3 shows exemplary MS spectrum of compound 9b.

FIG. 3 shows the MS spectrum of compound 9b.

Figure 4:
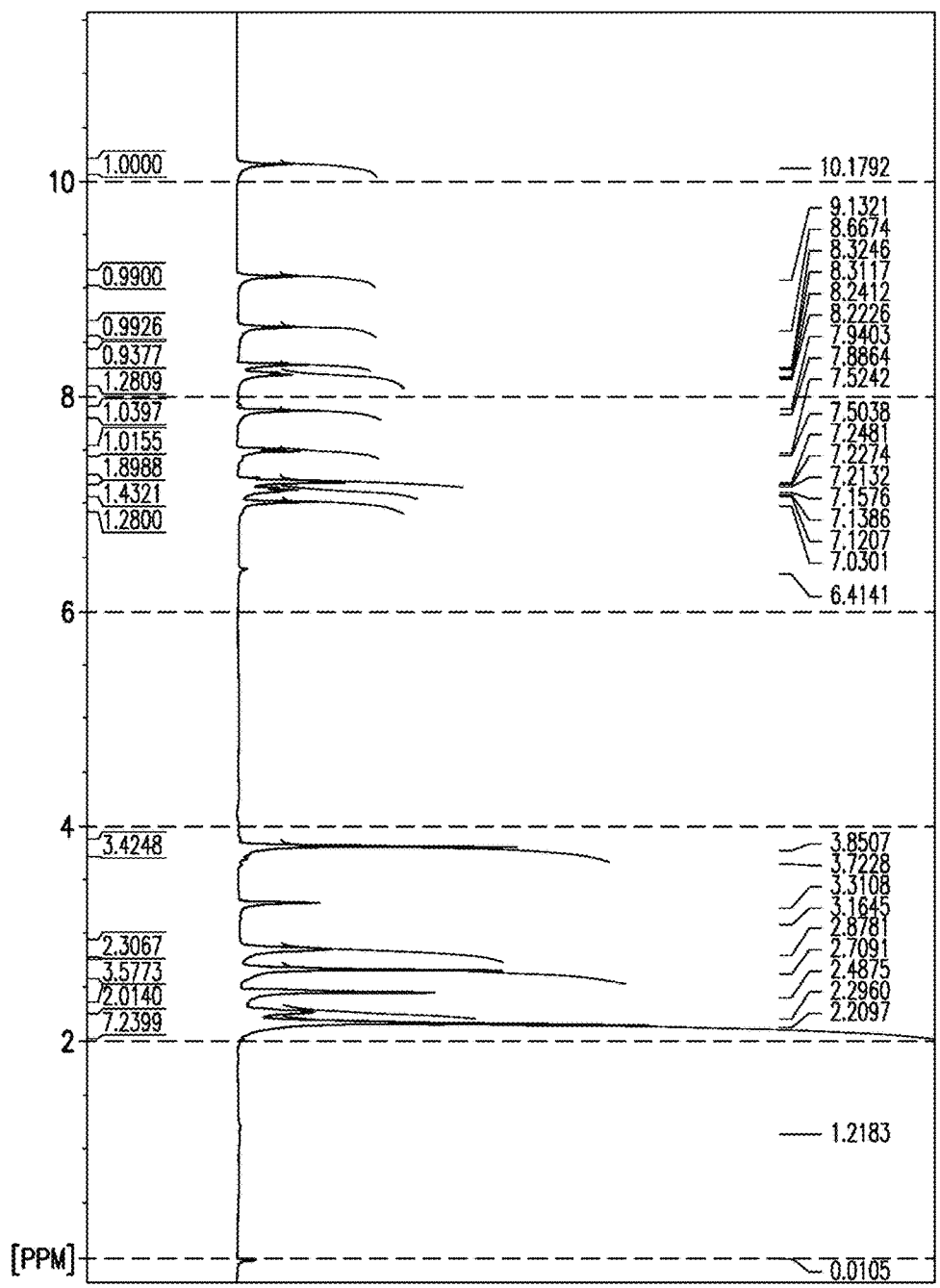
FIG. 4 shows exemplary $^1$H NMR spectrum of compound 9b.

FIG. 4 shows the ¹H NMR spectrum of compound 9b.

Compound 9c, $R_1=R_2=R_3=R_4=R_5=D$, $R_6=R_7=R_8=H$, $R_9=D$ (D16-Osimertinib)

Mass Spec: Mass Spec: $[M+H]^+=516.3$. ¹H-NMR (300 MHz, DMSO-d6): 10.19 (s, 1H), 9.10 (s, 1H), 8.65 (s, 1H), 8.31 (d, 1H), 8.23 (d, 1H), 7.89 (s, 1H), 7.51 (d, 1H), 7.22 (m, 2H), 7.15 (m, 1H), 7.02 (s, 1H), 6.44 (b, 1H), 6.26 (m, 1H), 5.76 (m, 1H), 3.85 (s, 3H); HPLC: 96.8% (AUC, 254 nm)

Figure 5:
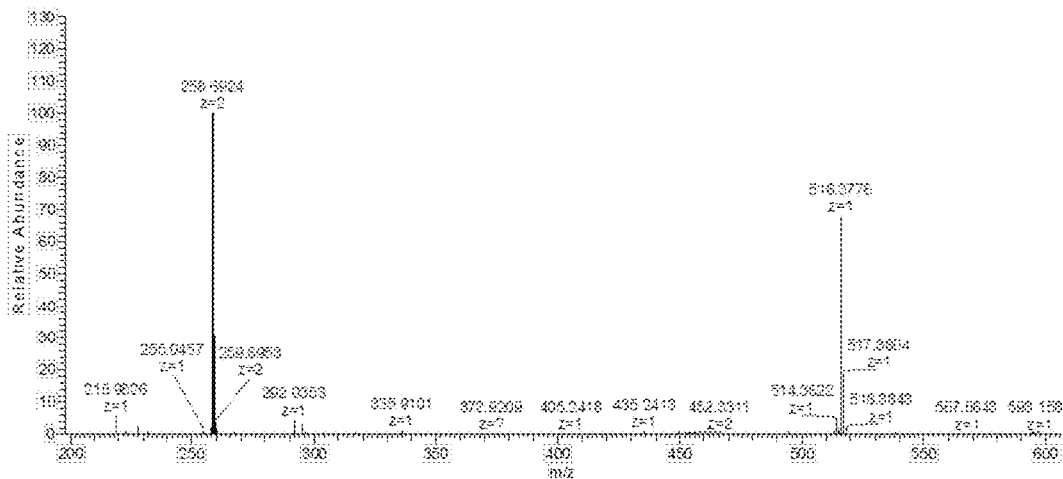
FIG. 5 shows exemplary MS spectrum of compound 9c.

FIG. 5 shows the MS spectrum of compound 9c.

Compound 9d, $R_1=R_2=R_3=R_4=R_5=R_6=R_7=R_8=R_9=D$ (D19-Osimertinib)

Mass Spec: $[M+H]^+=519.1$. ¹H-NMR (300 MHz, DMSO-d6): 10.19 (s, 1H), 9.10 (s, 1H), 8.65 (s, 1H), 8.31 (d, 1H), 8.23 (d, 1H), 7.89 (s, 1H), 7.51 (d, 1H), 7.22 (m, 2H), 7.15 (m, 1H), 7.02 (s, 1H), 3.85 (s, 3H); HPLC: 98.4% (AUC, 254 nm)

Figure 6:
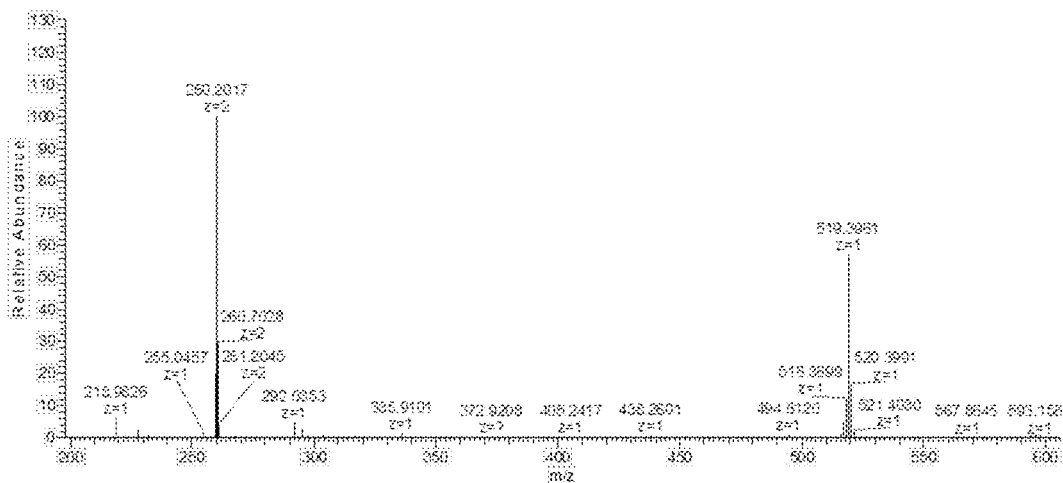
FIG. 6 shows exemplary MS spectrum of compound 9d.
Figure 7:
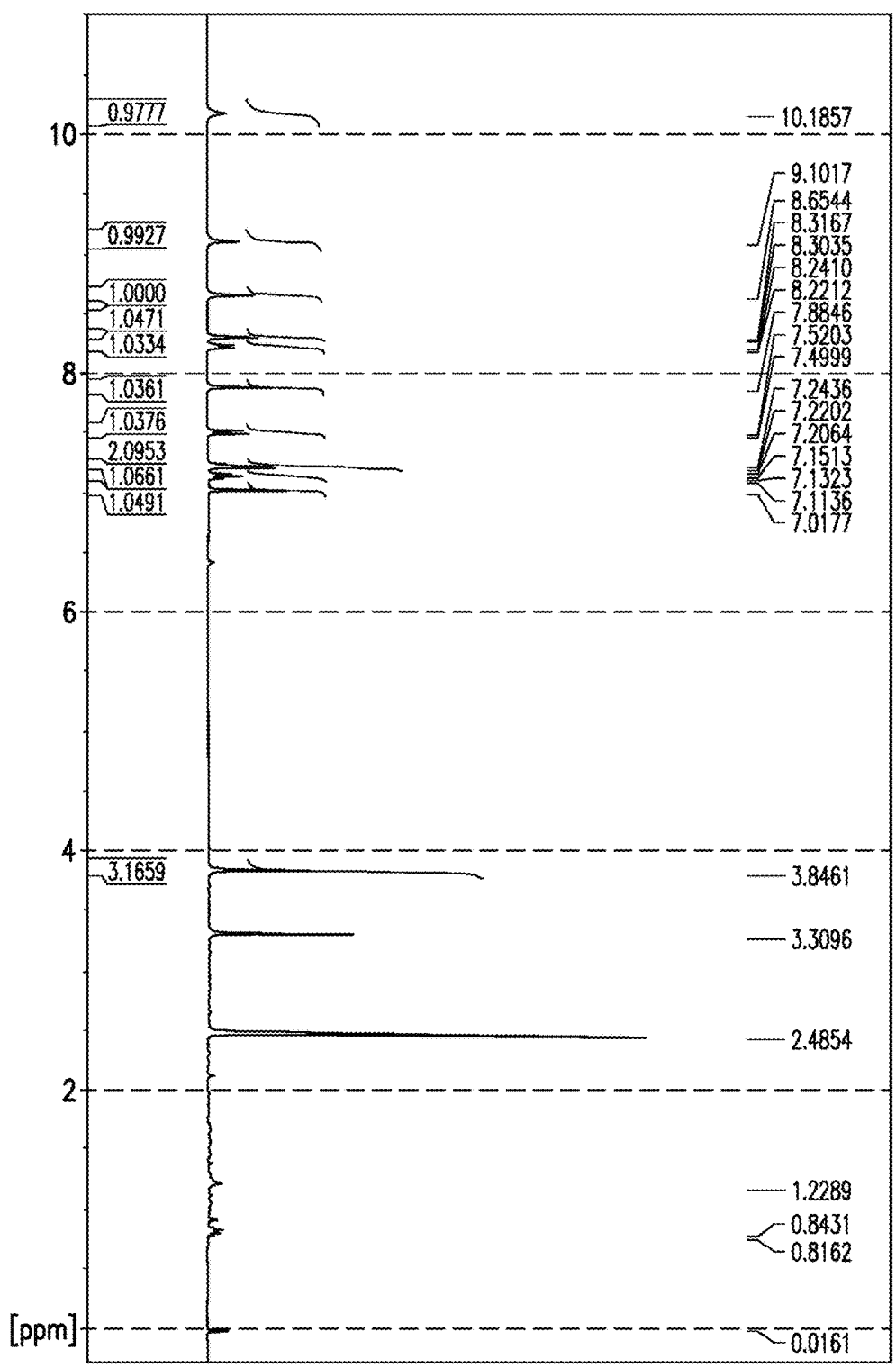
FIG. 7 shows exemplary $^1$H NMR spectrum of compound 9d.

FIG. 6 shows the MS spectrum of compound 9d.
FIG. 7 shows the ¹H NMR spectrum of compound 9d.

Drug Metabolism and Pharmacokinetic Evaluation By Human Microsome Experiment

In vitro drug metabolism and pharmacokinetic evaluation of D16-Osimertinib, and D19-Osimertinib against Osimertinib was conducted in Human Liver Microsome suspensions. The stability time course samples were prepared in house and extracted immediately by protein precipitation method using MeCN containing 400 ng/mL carbutomide as the internal standard (IS). The samples were analyzed on a Waters Acquity UPLC system coupled with a Bruker Q-tof mass spectrometer. The peak areas of respective extracted ion chromatograms were used for relative comparison.

The sample preparation was performed according to the following procedure: Three combo solutions in 100 mM potassium phosphate buffer pH=7.4 (contains 3.3 mM MgCl₂) were prepared. The combo solutions were (1) Osimertinib and D16-Osimertinib and (2) Osimertinib and D16-Osimertinib respectively. 300 μL of the above 2.0 μM combo solutions were added into 1.5 mL of Eppendof tubes. The samples were put in 37° C. incubator for 10 minutes. Then 300 μL of 37° C. pre-warmed 0.5 mg/mL of human liver microsome and 2.6 mM NADPH in 100 mM potassium phosphate buffer pH 7.4 (contains 3.3 mM MgCl2) was added to initiate the enzyme activity. 50.0 μL of the reaction mixture was put into 150 μL of MeCN with 400 ng/mL carbutamide (IS) to stop the reaction at 0', 15', 30', 60', 2 hours, 3 hours and 4 hours. The samples were vortexed and centrifuged at 13,000 g for approximately 5 minutes, then supernatants were taken and stored in −20° C. freezer. The sampling at a time point was triplicate. After the last samples were taken and they were placed in −20° C. at least 1 hour. All samples were put into a refrigerator at approximate 4° C. for 30 minutes. The samples were vortexed. Then approximately 100 μL of the supernatants were transferred to corresponding wells of a 96-well plate. The samples were diluted with 100 μL of 0.1% FA in water. The samples were vortexed and briefly centrifuged for LC-HRMS analysis. Sample chamber for LC-HRMS was kept at approximate 4° C.

Figure 8:
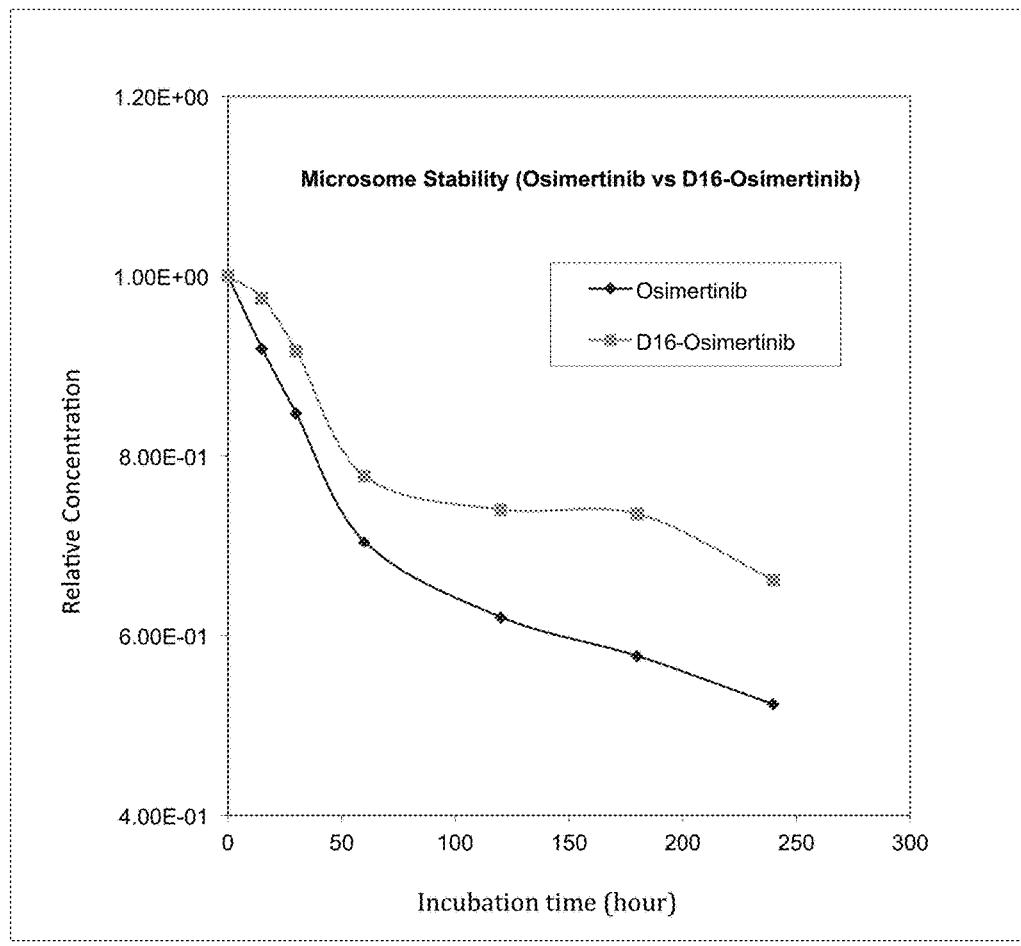
FIG. 8 shows exemplary results on percentage of compounds remaining vs. incubation time (Osimertinib vs D16-Osimertinib).
Figure 9:
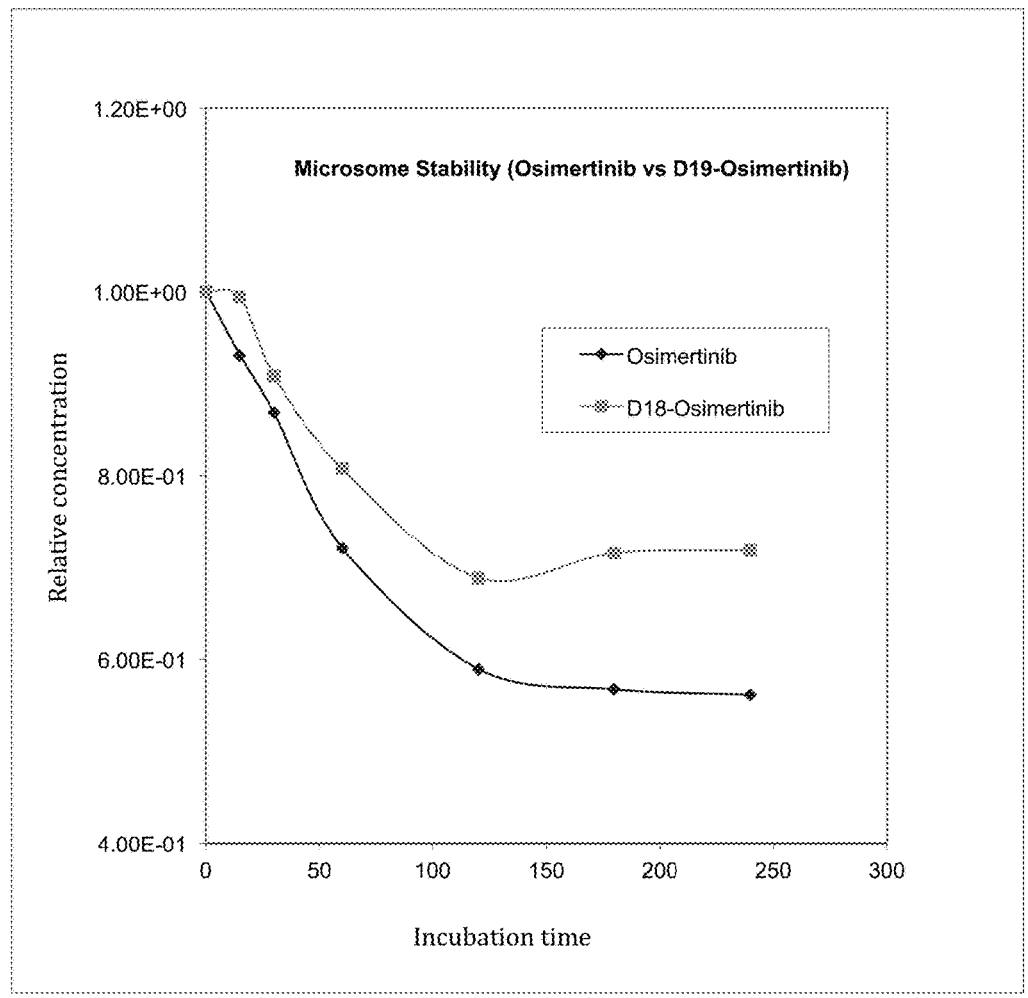
FIG. 9 shows exemplary results on percentage of compounds remaining vs. incubation time (Osimertinib vs D19-Osimertinib).
Figure 10:
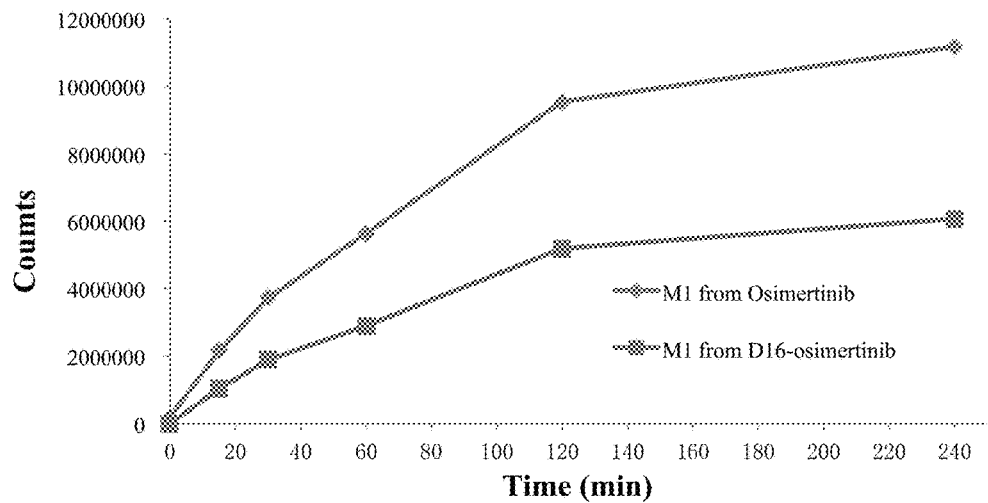
FIG. 10 shows exemplary data on the comparison of formation of de-methylation metabolite (M1) (Osimertinib and D16-Osimertinib).
Figure 11:
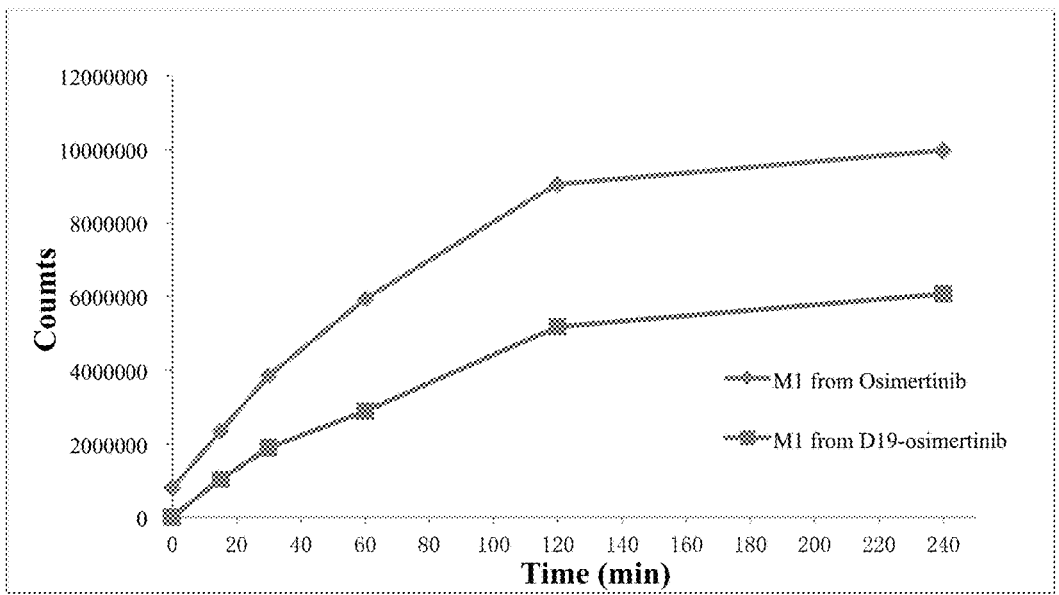
FIG. 11 shows exemplary data on the comparison of formation of de-methylation metabolite (M1) (Osimertinib and D19-Osimertinib).
Figure 12:
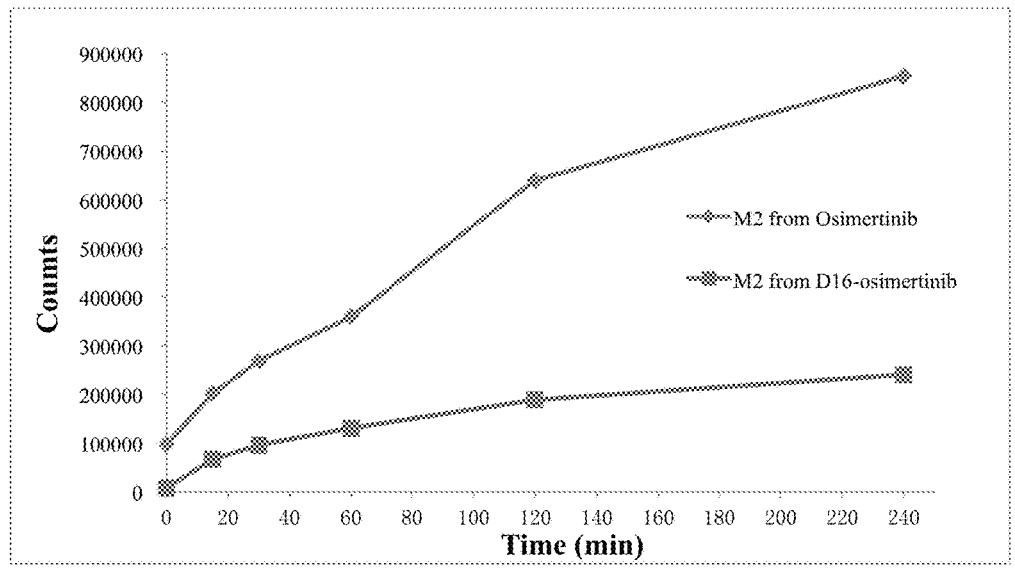
FIG. 12 shows exemplary data on the comparison of formation of Metabolite (M2) (Osimertinib and D16-Osimertinib).
Figure 13:
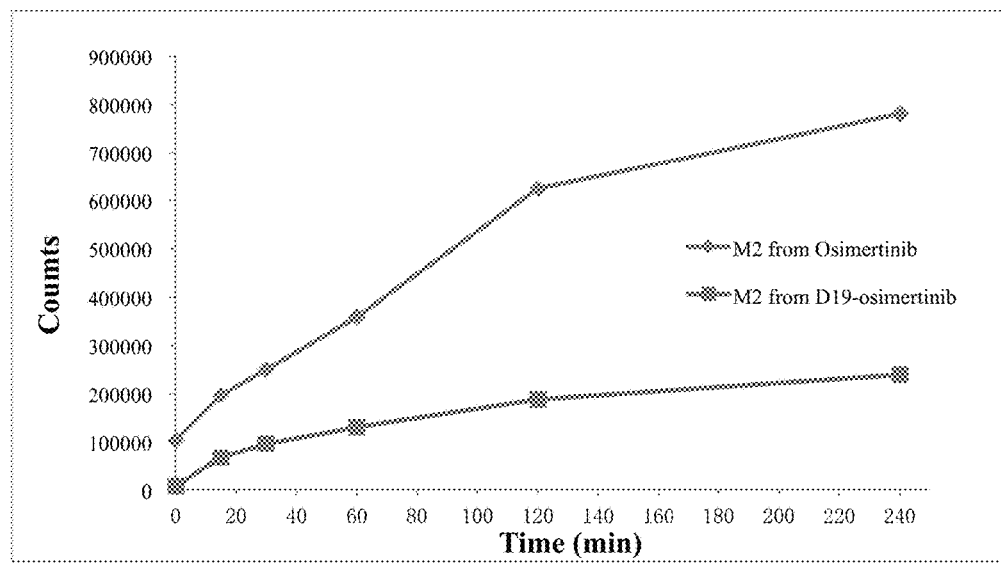
FIG. 13 shows exemplary data on the comparison of formation of Metabolite (M2) (Osimertinib and D19-Osimertinib).

FIG. 8 and FIG. 9 show the percentage of compounds remaining vs. incubation time. After 4 hour, the difference between the concentrations of Osimertinib and D16-Osimertinib was approximately equal to 26%. The difference between the concentrations of Osimertinib and D19-Osimertinib was approximately equal to 28%. The result showed that the selectively deuterated Osimertinib compounds have longer half-life and AUC. This substantial difference indicates superior DMPK property of selectively deuterated Osimertinib compounds that can lead to enhanced efficacy.

In vitro Evaluation of Toxic Metabolite (M1) and Reactive Metabolite (M2)

In vitro evaluation of D16-Osimertinib, and D19-Osimertinib against Osimertinib for formation of toxic metabolite with de-methylation at indole moiety (M1) and reactive metabolite (M2) was conducted in Human Liver Microsome suspensions. The stability time course samples were prepared in house and extracted immediately by protein precipitation method using MeCN having 400 ng/mL carbutomide as the internal standard (IS). The samples were analyzed on a Waters Acquity UPLC system coupled with a Thermo Scientific Q Exactive hybrid quadrupole-Orbitrap mass spectrometer. The peak areas of respective extracted ion chromatograms were used for relative comparison.

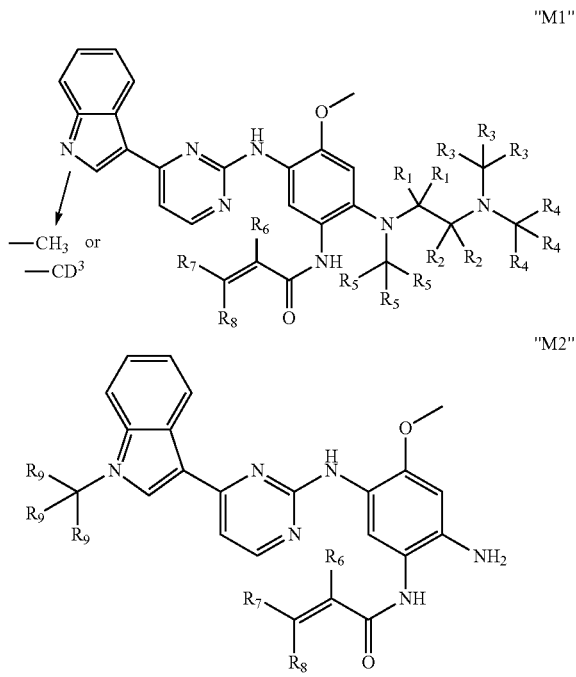

The sample preparation was performed according to the following procedure: three combo solutions in 100 mM potassium phosphate buffer pH=7.4 (contains 3.3 mM MgCl2) were prepared. The combo solutions were 1) Osimertinib and D16-Osimertinib and 2) Osimertinib and D19-Osimertinib respectively. 300 μL of the above 2.0 μM combo solutions were added into 1.5 mL of Eppendof tubes. The samples were put in 37° C. incubator for 10 minutes. Then 300 μL of 37° C. pre-warmed 0.5 mg/mL of human liver microsome and 2.6 mM NADPH in 100 mM potassium phosphate buffer pH 7.4 (contains 3.3 mM MgCl2) was added to initiate the enzyme activity. 50.0 μL of the reaction mixture was put into 150 μL of MeCN with 400 ng/mL carbutamide (IS) to stop the reaction at 0, 15, 30, 60, 120 and 240 minutes. The samples were vortexed and centrifuged at 13,000 g for approximately 5 minutes, then supernatants were taken and stored in −20° C. freezer. The sampling at a time point was triplicate. After the last samples were taken and they were placed in −20° C. at least 1 hour. All samples were put into a refrigerator at approximate 4° C. for 30 minutes. The samples were vortexed. Then approximately 100 μL of the supernatants were transferred to corresponding wells of a 96-well plate. The samples were diluted with 100 μL of 0.1% FA in water. The samples were vortexed and briefly centrifuged for LC-HRMS analysis. Sample chamber for LC-HRMS was kept at approximate 4 C.

The experimental data indicated that selective deuteration slowed down the formation of toxic metabolite (M1) and (M2).

FIGS. 10-13 show exemplary data on the comparisons of formation of metabolites (M1 and M2) from osimertinib and various deuterated osimertinib.

Cell-Based Experiment on Inhibition of WT-EGFR

As mentioned above, osimertinib has been shown to be potent to mutant EGFR. However, a demethylated metabolite of osimertinib, which exhibits a 5-fold more potency compared to osimertinib, shows a similar affinity towards wild-type EGFR. Thus, de-methylation at the indole position of osimertinib gives rise to a toxic metabolite, which has a higher affinity to wild-type EGFR and causes serious side effects during treatment. Such high affinity to wild-type EGFR raises serious safety issues and significantly limits the overall effectiveness of osimertinib in treating cancer patients.

Here, a cell-based experiment was designed to investigate the inhibition of wide-type EGFR containing cells using the osimertinib and deuterated osimertinib and the de-methylation metabolite (M1).

A431 cells are a model human cell line which express abnormally high levels of the wide-type epidermal growth factor receptor (WT EGFR). WT EGFR inhibitors can affect cell proliferation of the cells. Similarly the prolifiration of HepG2 hepatoma cells can be inhibited by WT EGFR inhibitors.

Experimental results indicated that osimertinib and selectively deuterated osimertinib compounds have high selectivity to A431 cells and HepG2 hepatoma. Both compounds did not affect the viability of cells. However, M1 significantly reduced the cell viability in both experiments with A413 cells and HepG2 hepatoma cells. These data confirmed the parent drugs inhibiting mutant EGFR do not hit the wide type EGFR while the metabolite M1 showed significate inhibition to wide-type EGFR. Therefore, M1 could have side effects that are caused by the inhibition of WT EFGR which raises serious safety issues. Avoiding the formation of this toxic metabolite is strongly desirable.

Figure 14:
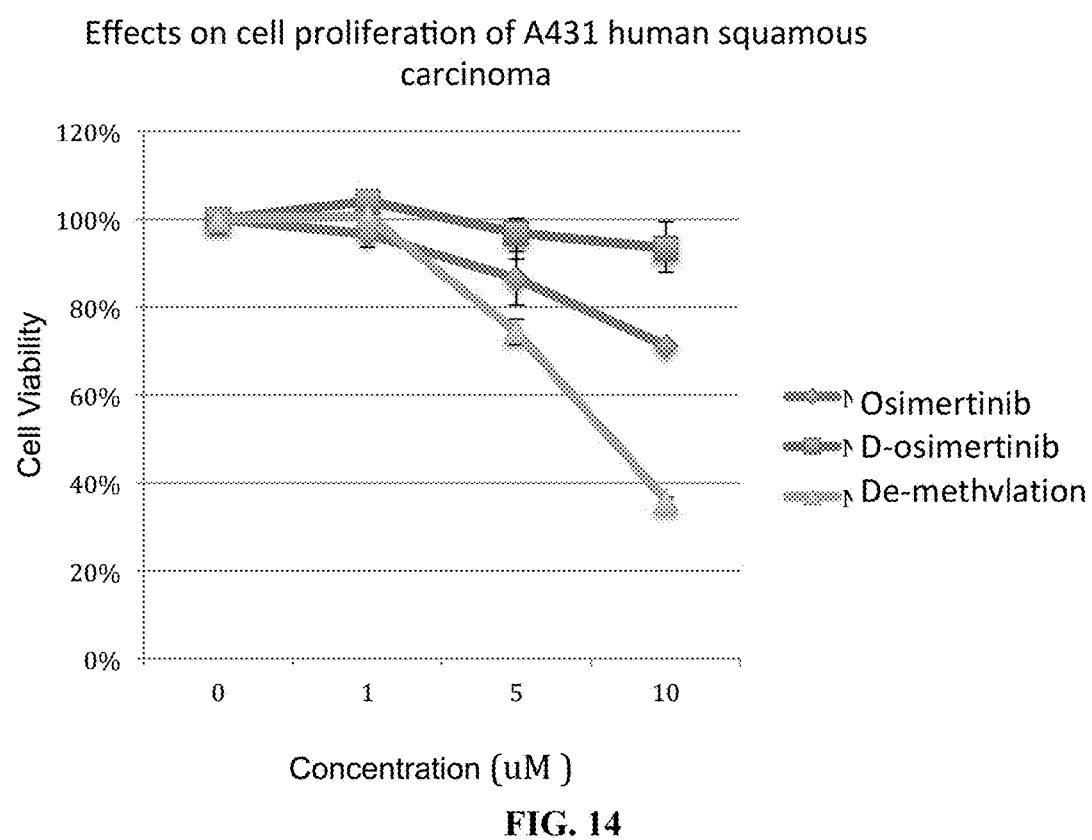
FIG. 14 shows exemplary data on the effect on cell proliferation of A431 human squamous carcinoma

FIG. 14 shows exemplary effects of cell proliferation of A431 human squamous carcinoma.

Figure 15:
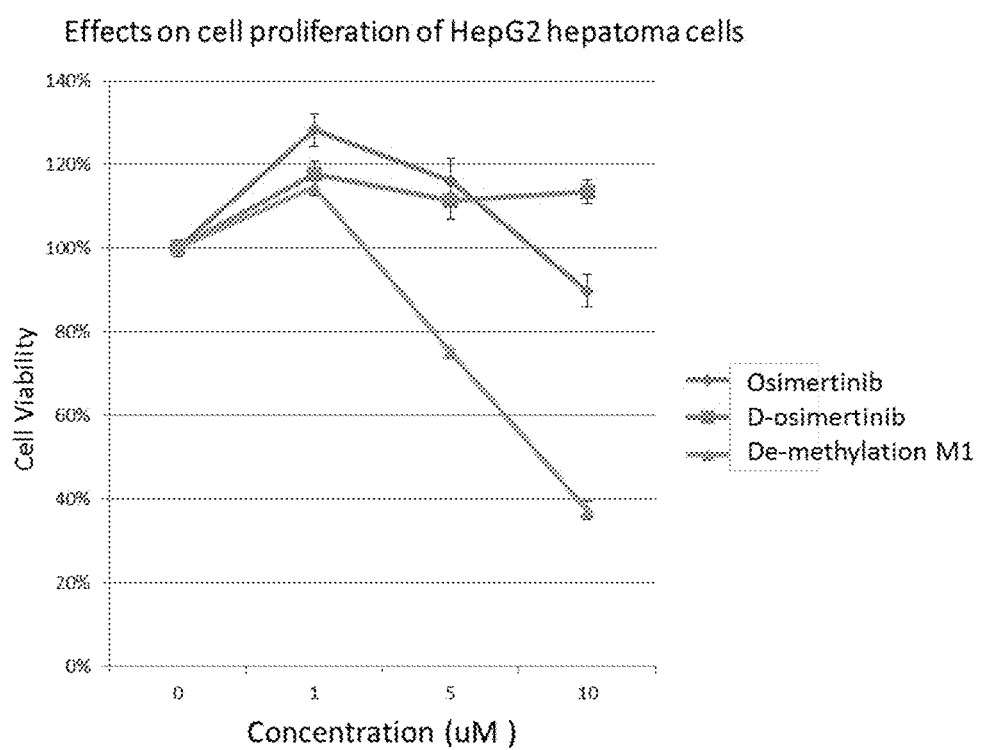
FIG. 15 shows exemplary data on the effect on cell proliferation pf HepG2 hepatoma cells.

FIG. 15 shows exemplary effects on cell proliferation of HepG2 hepatoma cells.

Bioactivity (IC50) Experiment

Osimertinib and deuterated Osimertinib compounds were tested in 10-dose IC50 mode with 3-fold serial dilution starting at 0.1 μM. Control Compound, Staurosporine, was tested in 10-dose IC50 mode with 4-fold serial dilution starting at 20 μM. Reactions were carried out at 2.5 μM ATP. The experiment results showed that the selective deuteration did not change IC-50 for the inhibition of EGFR T790M.

TABLE 1

| Kinase | [ATP](μM): | Compound IC50* (M): | | |
| --- | --- | --- | --- | --- |
| | | Osimertinib | D3-osimertinib | D6-osimertinib |
| EGFR (T790M) | 2.5 | 8.50E−10 | 7.74E−10 | 4.54E−10 |

TABLE 2

| Kinase | [ATP](μM): | Compound IC50* (M): | | |
|---|---|---|---|---|
| | | Osimertinib | D16-osimertinib | D19-osimertinib |
| EGFR (T790M) | 2.5 | 2.98E-10 | 3.34E-10 | 2.72E-10 |

Monkey Pharmacokinetic Study on Deuteration of Indole N-methyl Group

According to recent reports, in vivo rat, mouse and human studies showed the loss of the indole N-methyl group (—C(R$_9$)$_3$), which leads to significant quantities of a metabolite (M1).

Research has indicated that this metabolite with the loss of the methyl group to the indole selectivity decreases WT EGFR. Such high affinity to wild-type EGFR raises serious safety issues and significantly limits the overall effectiveness of osimertinib in treating cancer patients. Furthermore, the metabolite also increases IGF1R potency that might lead to hyperglycemia in human treatment. An objective of the invention is to reduce the de-methylation to the indole position. Selectively deuteration of the methyl group vcan achieves this goal.

A monkey pharmacokinetic study was performed to determine the pharmacokinetic parameters of osimertinib and dueterated osimertinib at the indole position and their metabolite of de-methylation (M1) in male cynomolgus monkeys following oral administrations.

A total of two (2) cynomolgus monkeys (male) were placed on study. Washout period lasted 7 days between two phases. Each test article was administered to an individual animal via a single oral administration for all groups. The dose levels were 20 mg/Kg. All animals were given detailed clinical examinations prior to administration, and no abnormality was observed. Cage side observation was conducted on all animals twice daily throughout the duration of administration. All animals were weighed before dosing on the day of administration. Blood samples were collected predose and postdose 0.25, 0.5, 1, 2, 3, 4, 6, 8, 12, 24, 36 and 48 h from the femoral vein at appropriate time points for analysis. These samples were analyzed by LC-MS/MS.

The experimental results indicated that under the condition of this study, after oral administration of Osimertinib, AUC(0-t) of the parent was 653.75 h*ng/mL. For Metabolite (M1), AUC(0-t) was 106.93 h*ng/mL. After oral administration of deuterated osimertinib, AUC(0-t) of the parent was 514.15 h*ng/mL. For Metabolite (M1), AUC(0-t) was 9.95 h*ng/mL.

Through selective deuteration, the formation toxic metabolite (M1) was significant reduced to 9.3% of osimertinib.

Figure 16:
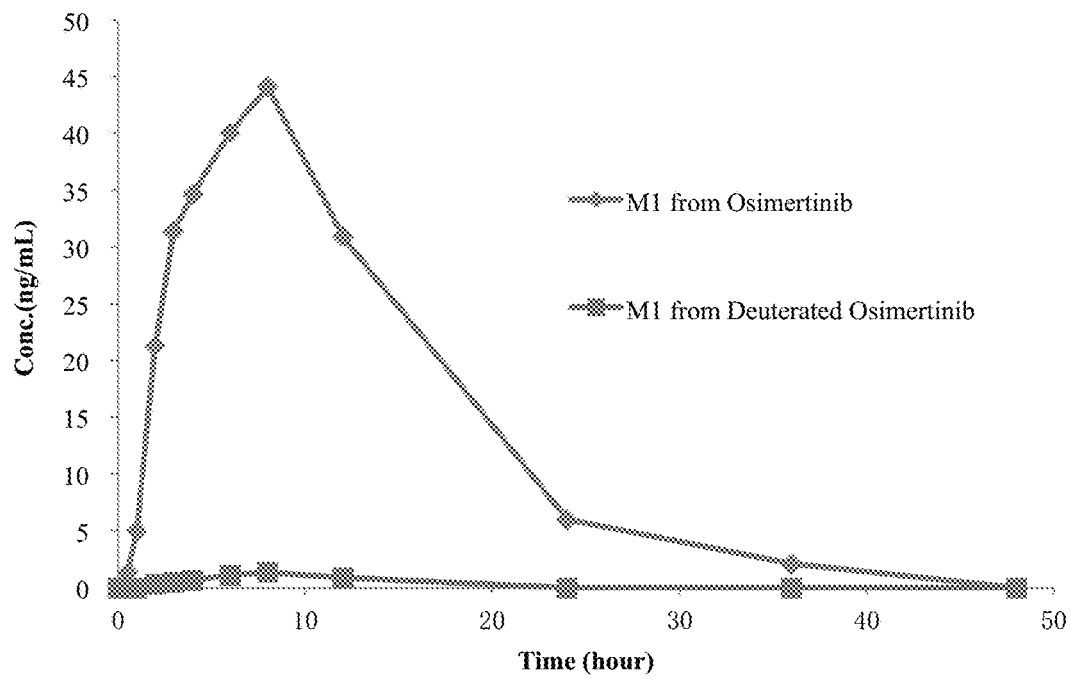
FIG. 16 shows exemplary data on metabolite (M1) concentration with de-methylation at indole moiety (Osimertinib and D3-Osimertinib).

FIG. 16 shows exemplary data on metabolite (M1) concentration with de-methylation at the indole moiety.

Improvement of Reactivity as Covalent Inhibitor to EGFR T790M

The compounds of covalent inhibitors bind to the EGFR kinase irreversibly by reacting with the cysteine-797 residue. The acrylamide moiety of the molecule serves as a chemically reactive Michael Acceptor (MA) electrophilic "warhead" which reacts with cysteine nucleophile to form an irreversible covalent adduct. The reactivity of forming covalent bonding contribute to the overall cellular inhibition of EGFR-T790M. The improvement of reactivity of the warhead moiety was proved enhanced cellular potency of compounds and is expected to ultimately increase efficacy in human treatment. Furthermore the improved reactivity may help to overcome drug resistance caused by cysteine oxidation.

The deuteration at the warhead of acrylamide moiety (R6, R7 and R8) showed unexpected effect in the improvement of reactivity.

The evaluation of the reactivity of D3-osimertinib, D6-osimertinib and D19-osimertinib against osimertinib was conducted in buffered aqueous system containing cysteine. The combo solutions were prepared by mixing individual evaluated compounds with reference osimertinib. Then, they were added to PBS buffer solution with cysteine at 37° C. The stability time course samples (in triplicate) were taken and added to prechilled quenching solution and then store at −70° C. freezer. The samples were analyzed on a Waters Acquity UPLC system coupled with a Bruker Q-tof mass spectrometer. The peak areas of respective extracted ion chromatograms were used for relative comparison.

The experimental data indicated that the reactivity was substantially increased when hydrogens in acrylamide moiety were replaced with deuteriums. The avaraged improvement of t1/2 of drug candidates was approximately 33%.

TABLE 3

Half-life of osimeritinib and deuterated compounds in cysteine solution

| Compound comparison | Reference (t½ h) | Deuterated (t½ h) | Improvement (%) |
|---|---|---|---|
| D3-osimertinib/Osimeritinib | 5.41 | 4.05 | 33 |
| D6-osimertinib/Osimeritinib | 5.62 | 4.56 | 23 |
| D19-osimertinib/Osimeritinib | 3.92 | 2.75 | 43 |

Figure 17:
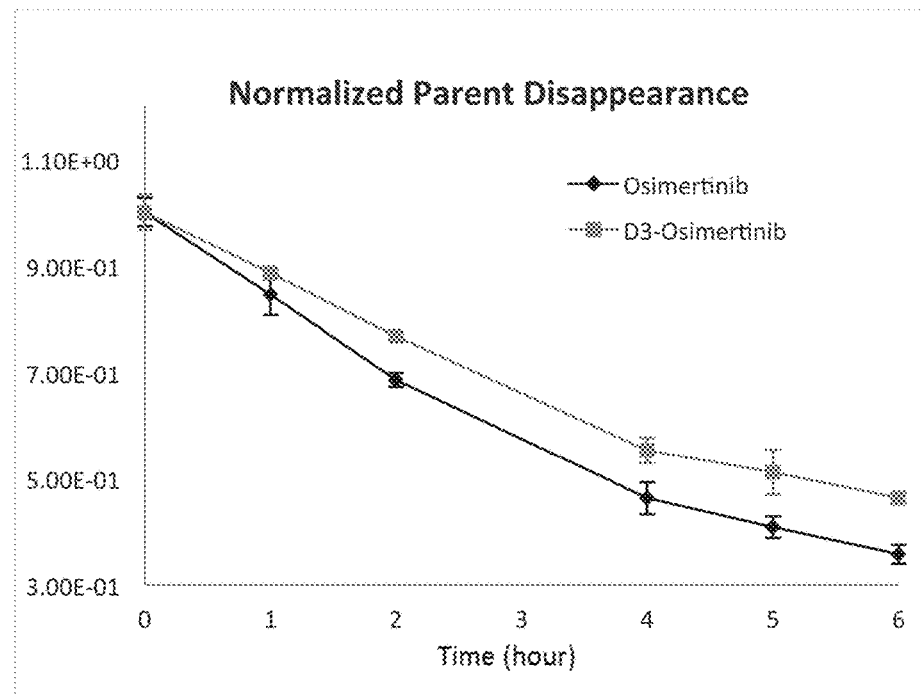
FIG. 17 shows exemplary data on normalized Parent Disappearance (Osimertinib and D3-Osimertinib).
Figure 18:
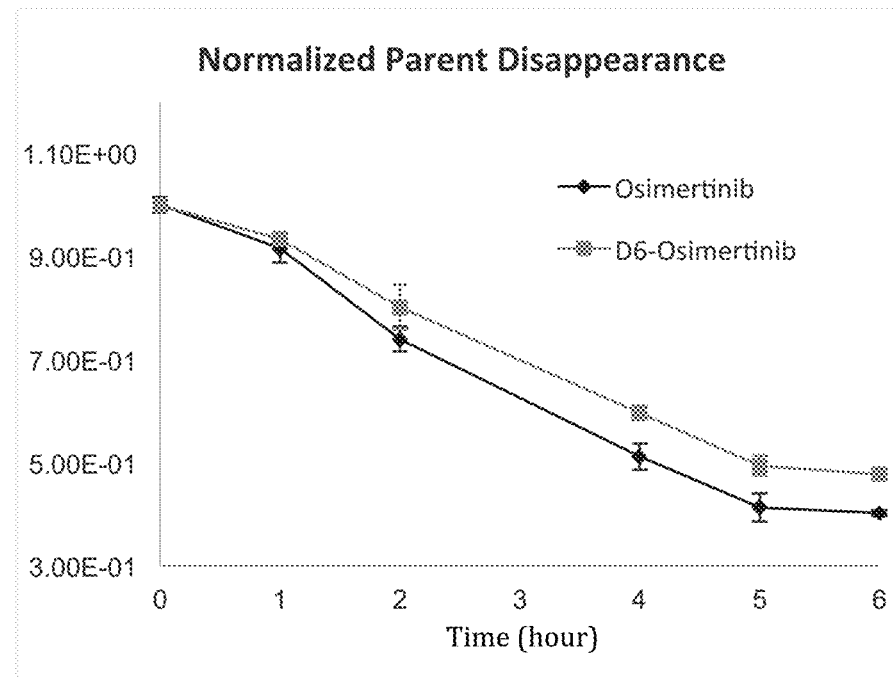
FIG. 18 shows exemplary data on normalized Parent Disappearance (Osimertinib and D6-Osimertinib).
Figure 19:
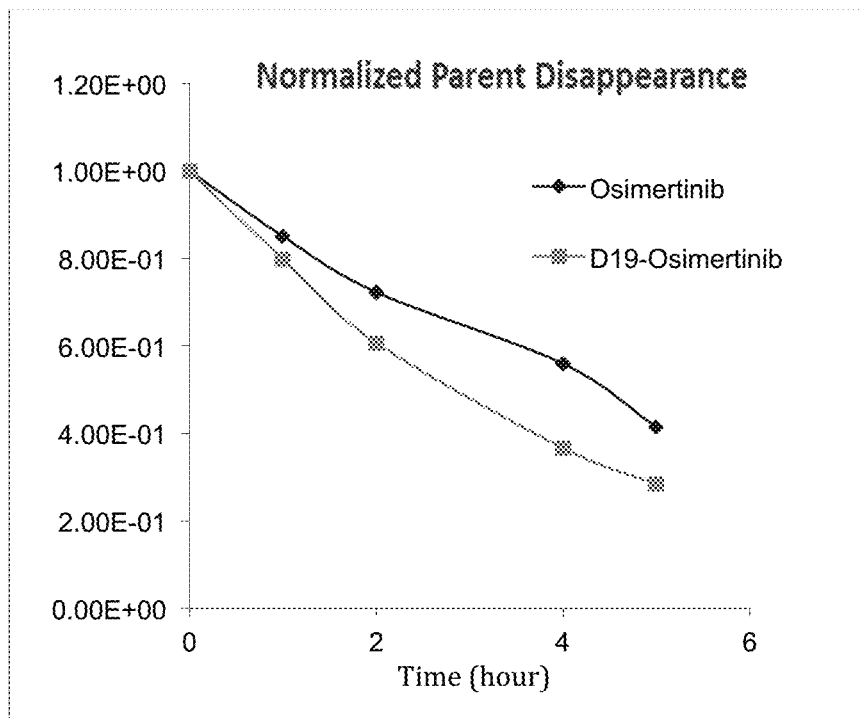
FIG. 19 shows exemplary data on normalized Parent Disappearance (Osimertinib and D19-Osimertinib).

FIGS. 17-19 show exemplary data on normalized parent disappearance of deuterated osimertinib as compared to the parent compound.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A compound having the structural formula of:

(I-B)

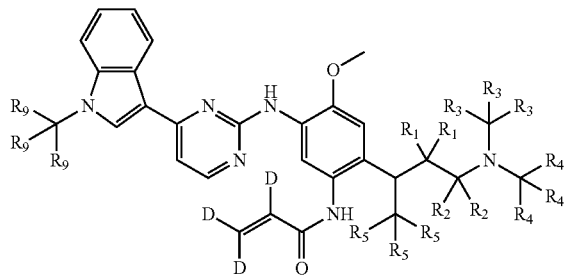

wherein each of $R_1$, $R_2$, $R_3$, $R_4$, $R_5$ and $R_9$ is independently selected from H and D, or a pharmaceutically acceptable form thereof.

2. The compound of claim 1, wherein each of $R_1$, $R_2$, $R_3$, $R_4$, $R_5$, and $R_9$ is H.

3. The compound of claim 1, wherein each of $R_1$, $R_2$, $R_3$, $R_4$ and $R_5$, is D and each $R_9$ is H.

4. The compound of claim 1, wherein $R_9$ is D, having the following structural formula, (II-A)

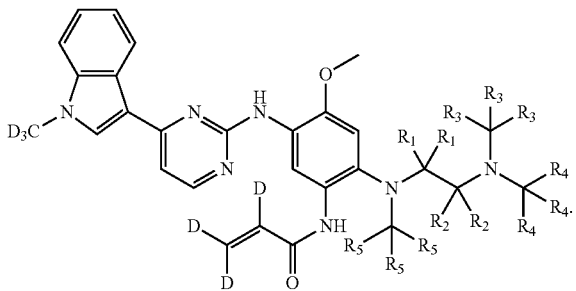

5. The compound of claim 4, wherein each of $R_1$, $R_2$, $R_3$, $R_4$ and $R_5$ is H.

6. The compound of claim 1, wherein each of $R_1$, $R_2$, $R_3$, $R_4$ and $R_5$ is D, having the following structural formula, (II-C)

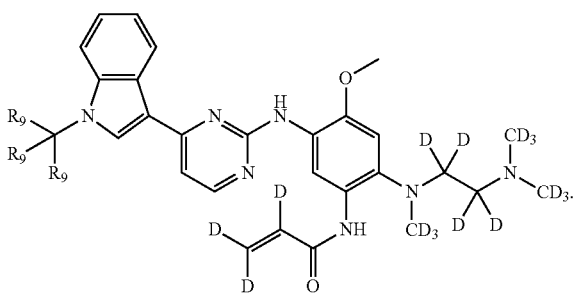

7. The compound of claim 1, wherein $R_1$, $R_2$, $R_3$, $R_4$, $R_5$, and $R_9$ is D, having the following structural formula,

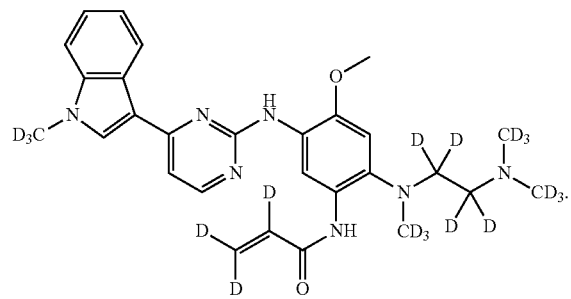 [SMILES: [2H]C([2H])=C([2H])C(=O)Nc1cc(Nc2nccc(-c3cn(C([2H])([2H])[2H])c4ccccc34)n2)c(OC)cc1N(C([2H])([2H])[2H])C([2H])([2H])C([2H])([2H])N(C([2H])([2H])[2H])C([2H])([2H])[2H]]

8. The compound of claim 1, wherein the compound is in the form of a mesylate salt.

9. A pharmaceutical composition comprising a compound having the structural formula of:

(I-B)

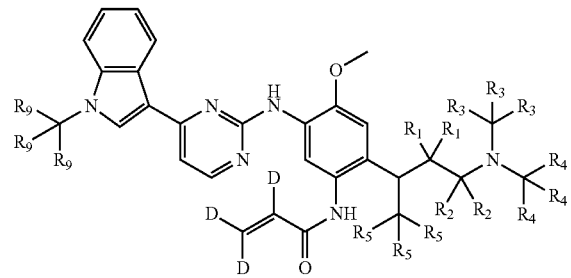

wherein each of $R_1$, $R_2$, $R_3$, $R_4$, $R_5$ and $R_9$ is independently selected from H and D, or a pharmaceutically acceptable form thereof, effective to treat cancer, or a related disease or disorder thereof, in a mammal, including a human, and a pharmaceutically acceptable excipient, carrier, or diluent.

10. The pharmaceutical composition of claim 9, wherein each of $R_1$, $R_2$, $R_3$, $R_4$, $R_5$, and $R_9$ is H.

11. The pharmaceutical composition of claim 9, wherein each of $R_1$, $R_2$, $R_3$, $R_4$ and $R_5$, is D and each $R_9$ is H.

12. The pharmaceutical composition of claim 9, wherein each of $R_9$ is D, having the following structural formula, (II-A)

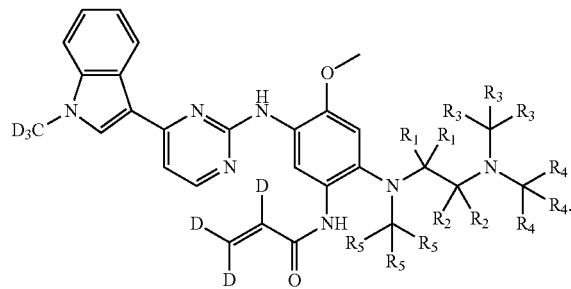

13. The pharmaceutical composition of claim 12, wherein each of $R_1$, $R_2$, $R_3$, $R_4$ and $R_5$ is H.

14. The pharmaceutical composition of claim 9, wherein each of $R_1$, $R_2$, $R_3$, $R_4$ and $R_5$ is D, having the following structural formula, (II-C)

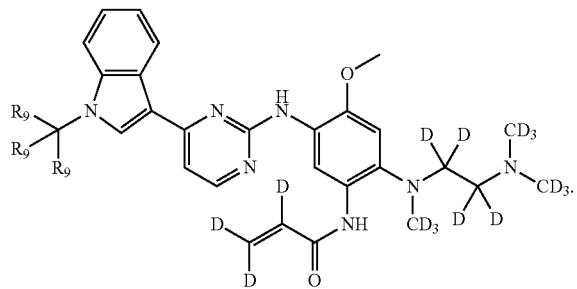

15. The pharmaceutical composition of claim 9, wherein $R_1$, $R_2$, $R_3$, $R_4$, $R_5$, and $R_9$ is D, having the following structural formula,

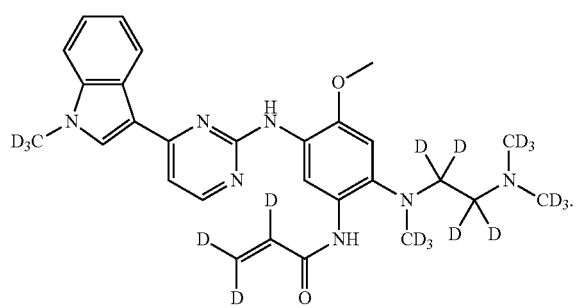

16. The pharmaceutical composition of claim 9, wherein the compound is in the form of a mesylate salt.

17. A unit dosage form comprising the pharmaceutical composition of claim 16.

18. A method for treating cancer or a related disease or disorder, comprising:

administering to a subject in need thereof a pharmaceutical composition comprising a compound having the formula of:

(I-B)

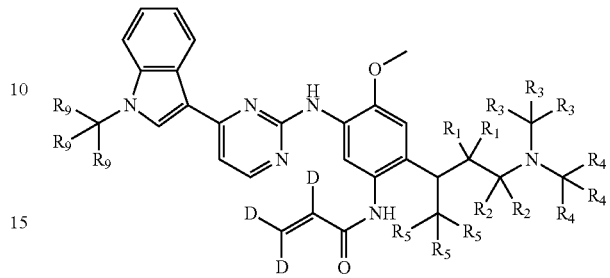

wherein each of $R_1$, $R_2$, $R_3$, $R_4$, $R_5$ and $R_9$ is independently selected from H and D, or a pharmaceutically acceptable form thereof.

19. The method of claim 18, wherein the cancer is lung cancer.

20. The method of claim 18, wherein the cancer is non-small cell lung cancer.

21. The method of claim 18, wherein the cancer is non-small cell lung cancer with EGFR T790M mutation.

22. The method of claim 18, wherein the pharmaceutical composition is administered to a subject with EGFRm+ and EGFR T790M mutation.

23. The method of claim 18, wherein each of $R_9$ is D, having the following structural formula, (II-A)

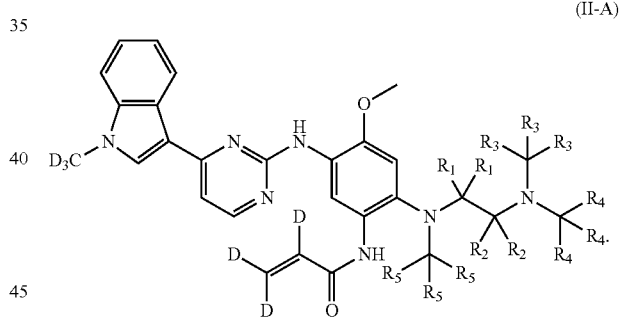

24. The method of claim 23, wherein each of $R_1$, $R_2$, $R_3$, $R_4$ and $R_5$ is H.

25. The method of claim 18, wherein each of $R_1$, $R_2$, $R_3$, $R_4$ and $R_5$ is D, having the following structural formula, (II-C)

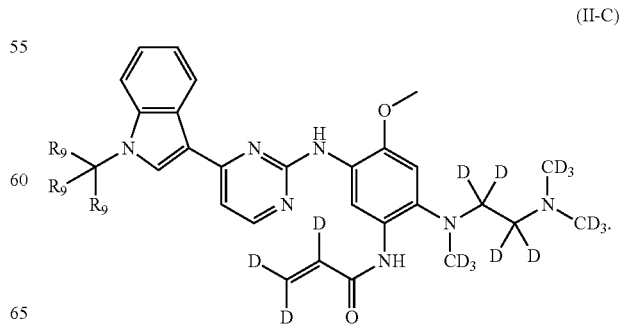

26. The method of claim 18, wherein $R_1$, $R_2$, $R_3$, $R_4$, $R_5$, $R_6$, $R_7$, $R_8$ and $R_9$ is D, having the following structural formula,

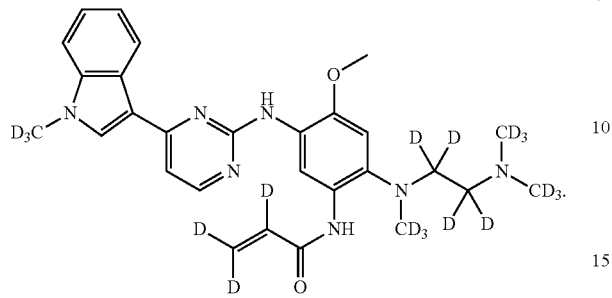

27. The method of claim 18, wherein the compound is in the form of a mesylate salt.

28. The method of claim 18, wherein the compound is administered in combination with one or more other anti-cancer agents selected from methotrexate, afatinib dimaleate, alectinib, pemetrexed disodium, bevacizumab, carboplatin, ceritinib, crizotinib, ramucirumab, docetaxel, erlotinib hydrochloride, methotrexate, gefitinib, gemcitabine hydrochloride, pembrolizumab, mechlorethamine hydrochloride, vinorelbine tartrate, necitumumab, nivolumab, paclitaxel, and erlotinib hydrochloride.

29. The method of claim 25, wherein each $R_9$ is H.

* * * * *